US009008780B2

(12) United States Patent
Nudo et al.

(10) Patent No.: US 9,008,780 B2
(45) Date of Patent: Apr. 14, 2015

(54) METHODS AND ASSOCIATED NEURAL PROSTHETIC DEVICES FOR BRIDGING BRAIN AREAS TO IMPROVE FUNCTION

(75) Inventors: Randolph J. Nudo, Overland Park, KS (US); David Guggenmos, Kansas City, KS (US); Pedram Mohseni, Highland Heights, OH (US); Meysam Azin, San Diego, CA (US)

(73) Assignees: Case Western Reserve University, Cleveland, OH (US); University of Kansas, Lawrence, KS (US)

( * ) Notice: Subject to any disclaimer, the term of this patent is extended or adjusted under 35 U.S.C. 154(b) by 0 days.

(21) Appl. No.: 13/523,597

(22) Filed: Jun. 14, 2012

(65) Prior Publication Data

US 2013/0090706 A1    Apr. 11, 2013

Related U.S. Application Data

(60) Provisional application No. 61/543,593, filed on Oct. 5, 2011.

(51) Int. Cl.
*A61N 1/05* (2006.01)
*A61N 1/36* (2006.01)
(Continued)

(52) U.S. Cl.
CPC .......... *A61N 1/36103* (2013.01); *A61B 5/6868* (2013.01); *A61N 1/0529* (2013.01); *A61N 1/0536* (2013.01); *A61N 1/0531* (2013.01); *A61B 5/04001* (2013.01); *A61N 1/36139* (2013.01)

(58) Field of Classification Search
CPC . A61N 1/0529; A61N 1/0531; A61N 1/0536; A61N 1/3605; A61N 1/36103; A61N 1/37205; A61B 5/04001; A61B 5/6868

USPC .................. 607/2, 45, 50, 62, 116, 117, 139; 600/378, 544, 545

See application file for complete search history.

(56) References Cited

U.S. PATENT DOCUMENTS 3,850,161 A * 11/1974 Liss ............................. 600/544
3,955,560 A * 5/1976 Stein et al. .................... 600/377
(Continued)

OTHER PUBLICATIONS

Azin, M.; Guggenmos, D.J.; Barbay, S.; Nudo, R.J.; Mohseni, P., "An activity-dependent brain microstimulation SoC with integrated 23nV/rtHz neural recording front-end and 750nW spike discrimination processor," VLSI Circuits (VLSIC), 2010 IEEE Symposium on, vol., No., pp. 223,224, Jun. 16-18, 2010.*

(Continued)

*Primary Examiner* — Carl H Layno
*Assistant Examiner* — Eugene Wu
(74) *Attorney, Agent, or Firm* — Workman Nydegger

(57) ABSTRACT

Methods for bridging brain sites between which there is substantially no effective communication, and associated neural prosthetic devices, are provided. A neural spike in a first neural site in a subject is detected, and a stimulus to a second neural site in the subject is delivered within a defined period of time after the detection of the neural spike, wherein there is substantially no effective communication between the first and second neural sites. The method forms an artificial bridge between the two neural sites, and establishes lasting communication between the two sites. The present disclosure provides, among other things, a neural prosthetic device comprising an integrated circuit that comprises a recording front-end comprising a plurality of recording channels; a processor unit; and a stimulus delivering back-end comprising a plurality of stimulation channels.

28 Claims, 22 Drawing Sheets

(51) Int. Cl.
A61B 5/00 (2006.01)
A61B 5/04 (2006.01)

(56) References Cited

U.S. PATENT DOCUMENTS

| | | | |
|---|---|---|---|
| 4,632,116 A * | 12/1986 | Rosen et al. | 607/62 |
| 5,030,225 A * | 7/1991 | Aebischer et al. | 606/152 |
| 5,048,522 A | 9/1991 | Petrofsky | |
| 7,010,351 B2 | 3/2006 | Firlik | |
| 7,092,763 B1 | 8/2006 | Griffith | |
| 7,991,465 B2 * | 8/2011 | Bartic et al. | 607/2 |
| 2005/0119703 A1 | 6/2005 | DiLorenzo | |
| 2005/0137648 A1* | 6/2005 | Cosendai et al. | 607/48 |
| 2005/0240242 A1 | 10/2005 | DiLorenzo | |
| 2005/0251221 A1* | 11/2005 | Zdravkovic | 607/46 |
| 2006/0009814 A1 | 1/2006 | Schulman | |
| 2006/0173259 A1 | 8/2006 | Flaherty et al. | |
| 2006/0200206 A1 | 9/2006 | Firlik et al. | |
| 2007/0032738 A1 | 2/2007 | Flaherty et al. | |
| 2007/0032834 A1 | 2/2007 | Gliner et al. | |
| 2007/0043401 A1* | 2/2007 | John | 607/45 |
| 2007/0112393 A1 | 5/2007 | Gliner | |
| 2007/0179584 A1 | 8/2007 | Gliner | |
| 2007/0282389 A1* | 12/2007 | Moxon et al. | 607/45 |
| 2009/0105786 A1* | 4/2009 | Fetz et al. | 607/48 |
| 2009/0112286 A1* | 4/2009 | Wang et al. | 607/50 |
| 2011/0009922 A1* | 1/2011 | Assaf et al. | 607/45 |
| 2012/0232631 A1* | 9/2012 | Frewin et al. | 607/116 |

OTHER PUBLICATIONS

Jackson, A.; Moritz, C.T.; Mavoori, J.; Lucas, T.H.; Fetz, E.E., "The neurochip BCI: towards a neural prosthesis for upper limb function," Neural Systems and Rehabilitation Engineering, IEEE Transactions on, vol. 14, No. 2, pp. 187,190, Jun. 2006.*

Azin, M.; Mohseni, P., "A high-output-impedance current microstimulator for anatomical rewiring of cortical circuitry," Circuits and Systems, 2008. ISCAS 2008. IEEE International Symposium on, vol., No., pp. 2502,2505, May 18-21, 2008.*

Mavoori. "An autonomous implantable computer for neural recording and stimulation in unrestrained primates." Journal of Neuroscience Methods 148: 71-77, 2005.*

Venkatraman, S.; Elkabany, K.; Long, J.D.; Yimin Yao; Carmena, J.M., "A System for Neural Recording and Closed-Loop Intracortical Microstimulation in Awake Rodents," Biomedical Engineering, IEEE Transactions on, vol. 56, No. 1, pp. 15,22, Jan. 2009.*

Azin, Meysam. "A battery powered multichannel microsystem for activity-dependent intracortical microstimulation." Thesis for PhD at Case Western Reserve University, May 2011.*

Zanos, S.; Richardson, A.G.; Shupe, L.; Miles, F.P.; Fetz, E.E., "The Neurochip-2: An Autonomous Head-Fixed Computer for Recording and Stimulating in Freely Behaving Monkeys," Neural Systems and Rehabilitation Engineering, IEEE Transactions on, vol. 19, No. 4, pp. 427,435, Aug. 2011.*

Azin, M.; Guggenmos, D.J.; Barbay, S.; Nudo, R.J.; Mohseni, P., "A Miniaturized System for Spike-Triggered Intracortical Microstimulation in an Ambulatory Rat," Biomedical Engineering, IEEE Transactions on, vol. 58, No. 9, pp. 2589,2597, Sep. 2011.*

Muller, Jan. "Sub-millisecond closed-loop feedback stimulation between arbitrary sets of individual neurons." Frontiers in Neural Circuits, vol. 6, Art 121, Jan. 2013.*

Stanslaski, S., et al., "Design and Validation of a Fully Implantable, Chronic, Closed-Loop Neuromodulation Device With Concurrent Sensing and Stimulation," *IEEE Transactions on Neural Systems and Rehabilitation Engineering*, vol. 20, No. 4, Jul. 2012, pp. 410-421.

M. M. Ahmadi, "A new modeling and optimization of gain-boosted cascode amplifier for high-speed and low-voltage applications," *IEEE Trans. Circuits Syst. II*, vol. 53, No. 3, pp. 169173, Mar. 2006.

A. T. Avestruz, W. Santa, D. Carlson, R. Jensen, S. Stanslaski, A. Helfenstine, and T. Denison, "A 5 11W/channel spectral analysis IC for chronic bidirectional brain-machine interfaces," *IEEE J. Solid-State Circuits*, vol. 43, No. 12, pp. 3006-3024, Dec. 2008.

T. W. Berger et al., "Restoring lost cognitive function: Hippocampalcortical neural prostheses," *IEEE Eng. Med. Biol. Mag.*, vol. 24, No. 5, pp. 30-44, Sep./Oct. 2005.

P. K. Campbell, K. E. Jones, R. J. Huber, K. W. Horch, and R. A. Normann, "A silicon-based, three-dimensional neural interface: Manufacturing process for an intracortical electrode array," *IEEE Trans. Biomed. Eng.*, vol. 38, pp. 758-767,1991.

M. S. Chae, Z. Yang, M. R. Yuce, L. Hoang, and W. Liu, "A 128-channel 6-mW wireless neural recording IC with spike feature extraction and UWB transmitter," *IEEE Trans. Neural Syst. Rehab. Eng.*, vol. 17, No. 4, pp. 312-321, Aug. 2009.

T. Chen, K. Chen, Z. Yang, K. Cockerham, and W. Liu, "A biomedical multiprocessor SoC for closed-loop neuroprosthetic applications," in *IEEE Int. Solid State Circuits Conference (ISSCC'09) Dig. Tech. Papers*, San Francisco, CA, Feb. 8-12, 2009, pp. 434-435.

T. G. Constandinou, J. Georgiou, and C. Toumazou, "A partial-current-steering biphasic stimulation driver for vestibular prostheses," *IEEE Trans. Biomed. Circuits Syst.*, vol. 2, No. 2, pp. 106-113, Jun. 2008.

T. Denison, K. Consoer, W. Santa, A.-T. Avestruz, J. Cooley, and A. Kelly, "A 2 □ W 100 nV/rtHz chopper-stabilized instrumentation amplifier for chronic measurement of neural field potentials," *IEEE J. Solid-State Circuits*, vol. 42, No. 12, pp. 2934-2945, Dec. 2007.

X. J. Feng, B. Greenwald, H. Rabitz, E. Shea-Brown, and B. Kosut, "Toward closed-loop optimization of deep brain stimulation for Parkinson's disease: Concepts and lessons from a computational model," *J. Neural Eng.*, vol. 4, pp. L14-L21,2007.

M. Ghovanloo and K. Najafi, "A compact large-voltage-compliance high-outputimpedance programmable current source for implantable microstimulators," *IEEE Trans. Biomed. Eng.*, vol. 52, No. 1, pp. 97-105, Jan. 2005.

R. R. Harrison and C. Charles, "A low-power low-noise CMOS amplifier for neural recording applications," *IEEE J. Solid-State Circuits*, vol. 38, No. 6, pp. 958-965, Jun. 2003.

L. R. Hochberg, M. D. Serruya, G. M. Friehs, J. A. Mukand, M. Saleh, A. FL Caplan, A. Branner, D. Chen, R. D. Penn, and J. P. Donoghue, "Neuronal ensemble control of prosthetic devices by a human with tetraplegia," *Nature*, vol. 442, pp. 164-171, Jul. 2006.

A. Jackson, J. Mavoori, and E. E. Fetz, "Long-term motor cortex plasticity induced by an electronic neural implant," *Nature*, vol. 444, pp. 56-60, Nov. 2006.

A. Keller and H. Asanuma, "Synaptic relationships involving local axon collaterals of pyramidal neurons in the cat motor cortex," *J. Comp. Neurol.*, vol. 336, pp. 229-242,1993.

J. Lee, H. G. Rhew, D. R. Kipke, and M. P. Flynn, "A 64-channel programmable closed-loop neurostimulator with 8-channel neural amplifier and logarithmic ADC," *IEEE J. Solid-State Circuits*, vol. 45, No. 9, pp. 1935-1945, Sep. 2010.

X. Liu, A. Demosthenous, and N. Donaldson, "An integrated implantable stimulator that is fail-safe without off-chip blocking capacitors," *IEEE Trans. Biomed. Circuits Syst.*, vol. 2, No. 3, pp. 231-244, Sep. 2008.

D. J. McFarland and J. R. Wolpaw, "Brain-computer interface operation of robotic and prosthetic devices," *Computer*, vol. 41, No. 10, pp. 52-56, Oct. 2008.

M. Mollazadeh, K. Murari, G. Cauwenberghs, and N. Thakor, "Micropower CMOSintegrated low-noise amplification, filtering, and digitization of multimodal neuropotentials," *IEEE Trans. Biomed. Circuits Syst.*, vol. 3, No. 1, pp. 1-10, Feb. 2009.

C. T. Moritz, S. I. Perlmutter, and E. E. Fetz, "Direct control of paralyzed muscles by cortical neurons," *Nature*, vol. 456, pp. 639-643,2008.

M. A. L. Nicolelis, A. A. Ghazanfar, B. M. Faggin, S. Votaw, and L. M. 0. Oliveira, "Reconstructing the Engram: Simultaneous, multisite, many single neuron recordings," *Neuron*, vol. 18, pp. 529-537, Apr. 1997.

M. Nishibe, S. Barbay, D. Guggenmos, and R. J. Nudo, "Reorganization of motor cortex after cortical impact in rats and implications for functional recovery," *J. Neurotrauma*, vol. 27, pp. 2221-2232, Dec. 2010.

(56) References Cited

OTHER PUBLICATIONS

M. Ortmanns, A. Rocke, M. Gehrke, and H. J. Tiedtke, "A 232-channel epiretinal stimulator ASIC," *IEEE J. Solid-State Circuits*, vol. 42, No. 12, pp. 2946-2959, Dec. 2007.

J. P. Rauschecker and R. V. Shannon, "Sending sound to the brain," *Science*, vol. 295, No. 5557, pp. 1025-1029, Feb. 2002.

F. Shahrokhi, K. Abdelhalim, D. Serletis, P. L. Carlen, and R. Genov, "The 128-channel fully differential integrated neural recording and stimulation interface," *IEEE Trans. Biomed. Circuits Syst.*, vol. 4, No. 3, pp. 149-161, Jun. 2010.

J. J. Sit and R. Sarpeshkar, "A low-power blocking-capacitor-free charge-balanced electrode-stimulator chip with less than 6 nA dc error for 1-mA full-scale stimulation," *IEEE Trans. Biomed. Circuits Syst.*, vol. 1, No. 3, pp. 172-183, Sep. 2007.

A. M. Sodagar, G. E. Perlin, Y. Yao, K. Najafi, and K. D. Wise, "An implantable 64-channel wireless microsystem for single-unit neural recording," *IEEE J. Solid-State Circuits*, vol. 44, No. 9, pp. 2591-2604, Sep. 2009.

K. Sooksood, T. Stieglitz, and M. Ortmanns, "An active approach for charge balancing in functional electrical stimulation," *IEEE Trans. Biomed. Circuits Syst.*, vol. 4, No. 3, pp. 162-170, Jun. 2010.

Y. Tsividis, *Operation and Modeling of the MOS Transistor*, 2nd ed. New York, NY: Oxford Univ. Press, 1999.

B. K. Thurgood, D. J. Warren, N. M. Ledbetter, G. A. Clark, and R. R. Harrison, "A wireless integrated circuit for 100-channel charge-balanced neural stimulation," *IEEE Trans. Biomed. Circuits Syst.*, vol. 3, No. 6, pp. 405-414, Dec. 2009.

M. Velliste, S. Perel, M. C. Spalding, A. S. Whitford, and A. B. Schwartz, "Cortical control of a prosthetic arm for self-feeding," *Nature*, vol. 453, pp. 1098-1101, Jun. 2008.

Mavoori, et al. "An Autonomous implantable computer for neutral recording and stimulation in unrestrained primates." Journal of Neuroscience Methods 148 (2005) 71-77.

Ghez, Claude, Voluntary Movement, *Principles of Neural Science*. Kandel, et al (Eds.), Sep. 2001, pp. 609-613, Elsevier, New York, New York.

\* cited by examiner

METHODS AND ASSOCIATED NEURAL PROSTHETIC DEVICES FOR BRIDGING BRAIN AREAS TO IMPROVE FUNCTION

CROSS REFERENCE TO RELATED APPLICATIONS

This application claims priority to U.S. Provisional Application No. 61/543,593, filed Oct. 5, 2011, which is incorporated herein by reference.

STATEMENT OF GOVERNMENT INTEREST

This invention was made with government support under Grant Nos. W81XWH-08-1-0168, W81XWH-10-1-0741, and W81XWH-10-1-0742 awarded by the Department of Defense. The government has certain rights in the invention.

BACKGROUND

To date, brain-machine interfaces (BMIs) have sought to interface the brain with the external world using intrinsic neuronal signals as input commands for controlling external devices, or device-generated electrical signals to mimic sensory inputs to the nervous system. A new generation of neuroprostheses is now emerging that aims to combine neural recording, neural signal processing, and microstimulation functionalities in a single device, creating an artificial connection in the nervous system by converting neural activity recorded from one cortical area to electrical stimuli delivered to another cortical area, spinal cord, or muscles in real time.

SUMMARY

The present disclosure generally relates to methods and associated neural prosthetic devices for bridging brain areas for the purpose of restoring or improving neurological function. More particularly, the present disclosure relates to, in one embodiment, multi-channel neural prosthetic devices and, in other embodiments, methods for utilizing a neural prosthetic device to function as a bridge between two neural sites between which there is substantially no effective communication.

The present disclosure provides neural prosthetic devices (i.e., microdevices) that successfully combine neural recording, signal processing, and microstimulation functionalities in a single device for closed-loop operation. Further, the present disclosure provides neural prosthetic devices that can operate autonomously and that convert extracellular neural signals recorded on one microelectrode to electrical stimuli delivered via another electrode in real time. In some embodiments, the methods of the present disclosure promote functional recovery after brain injury and are particularly suitable for reestablishing communication links between remote neural regions.

The devices and methods of the present disclosure may also be useful to provide activity-dependent neural stimulation to induce neuronal plasticity for functional reorganization in an intact nervous system, and have numerous applications such as restoring function after neuronal injury, providing refined sensory inputs in neuroprosthetic systems or supporting closed-loop therapeutic interventions for neuropathologies.

Accordingly, in one embodiment, the present disclosure provides a method comprising detecting a neural spike in a first neural site in a subject; and delivering a stimulus to a second neural site in the subject within a defined period of time after the detection of the neural spike, wherein there is substantially no effective communication between the first and second neural sites.

In another embodiment, the present disclosure provides a neural prosthetic device comprising an integrated circuit that comprises a recording front-end comprising a plurality of recording channels; a processor unit; and a stimulus delivering back-end comprising a plurality of stimulation channels.

In yet another embodiment, the present disclosure provides a method comprising providing a subject having a brain injury in which there is substantially no effective communication between a first neural site in the subject and a second neural site in the subject; detecting a neural spike in the first neural site; using a neural prosthetic device comprising a recording front-end, a processor unit, and a stimulus delivering back-end to deliver an electrical stimulus to the second neural site within a defined period of time after the detection of the neural spike; and allowing the neural prosthetic device to provide an effective communication bridge between the first and second neural sites.

The features and advantages of the present invention will be apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings.

Figure 3:
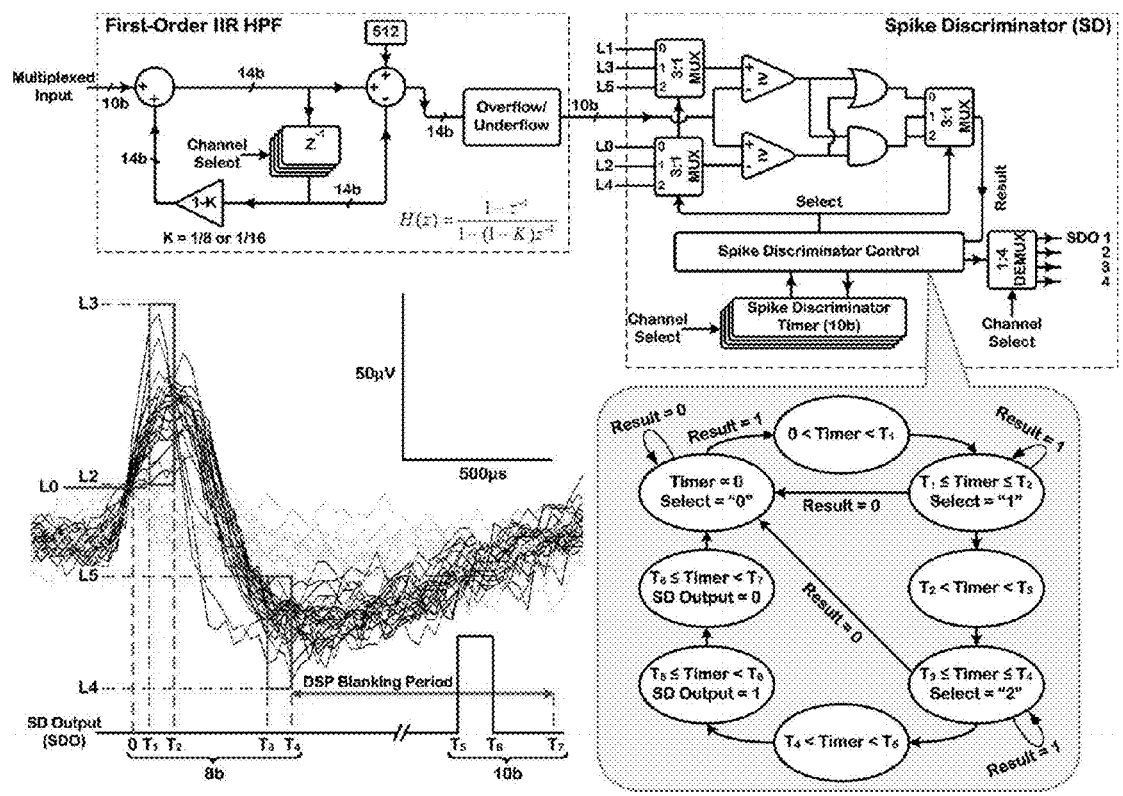

FIG. 3 depicts the architecture of a digital signal processing (DSP) unit and operation of a time-amplitude window discriminator in a neural prosthesis suitable for use in the methods of the present disclosure. The flow chart for spike discrimination algorithm is also shown. Negative threshold level $L_1$ (not shown in bottom left) is used in the algorithm to discriminate waveforms with reverse polarity (i.e., negative-going initial portion), if necessary.

Figure 4:
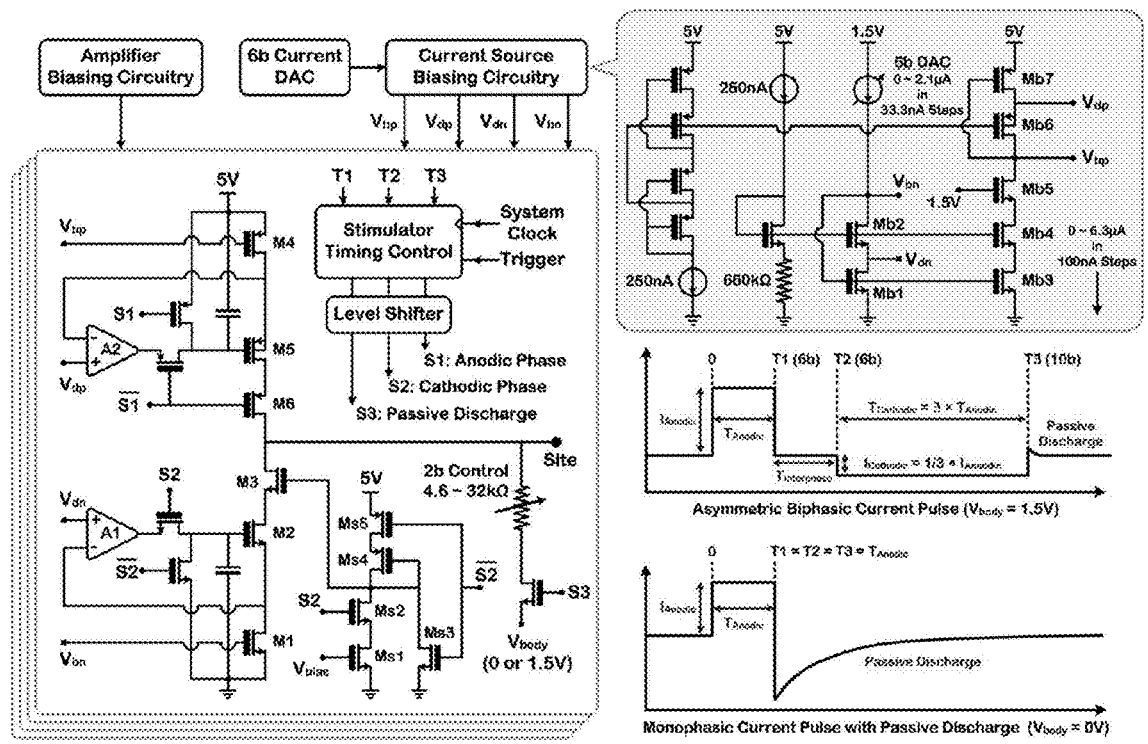

FIG. 4 is a circuit schematic of the microstimulating back-end of one channel in a neural prosthesis suitable for use in the methods of the present disclosure.

Figure 5:
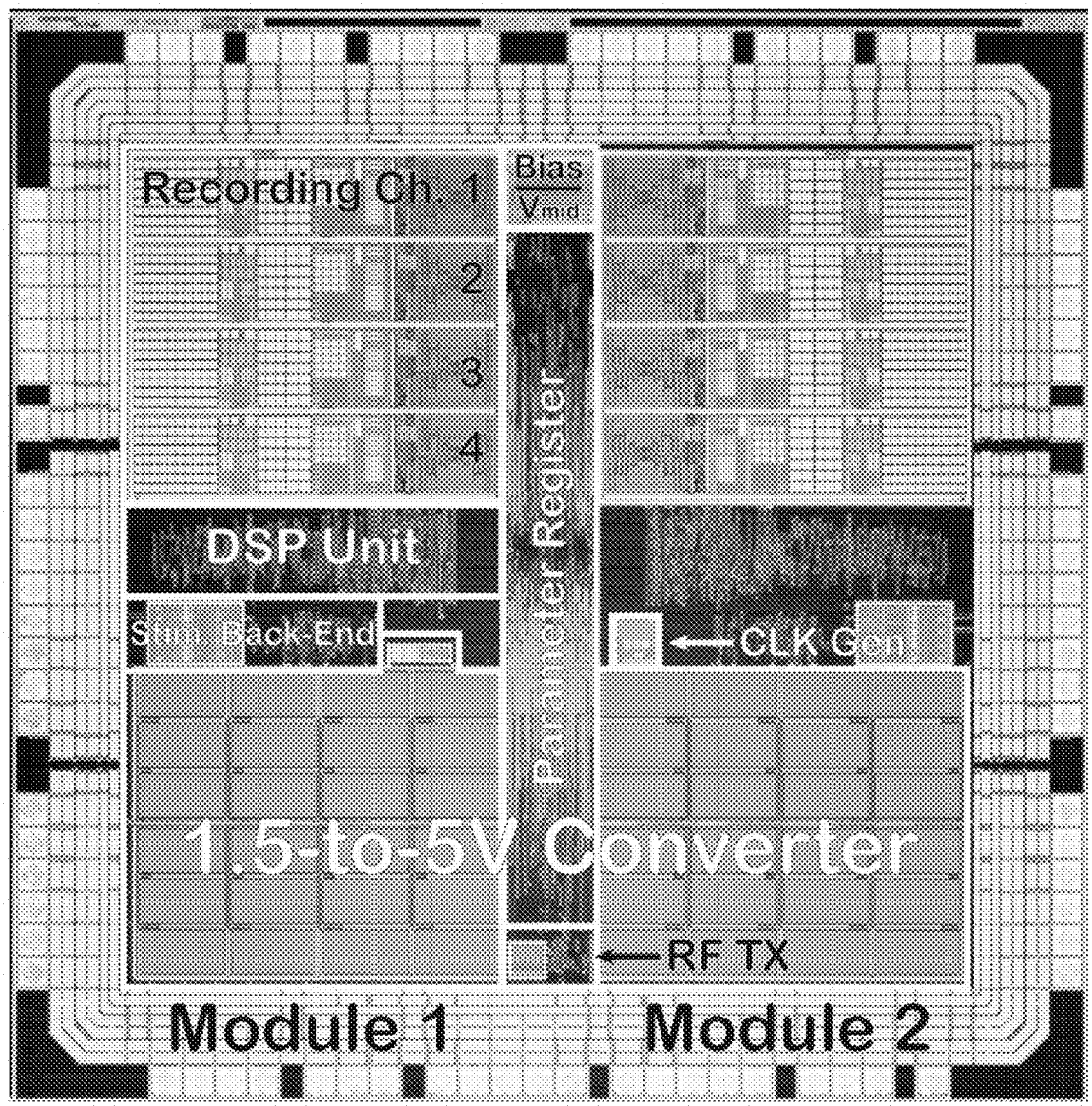

FIG. 5 is a die micrograph of a 3.3 mm×3.3 mm integrated circuit (IC) fabricated in 0.35-μm two-poly four-metal (2P/4M) complementary metal-oxide-semiconductor (CMOS) technology.

Figures 6A, 6B, 6C, 6D:
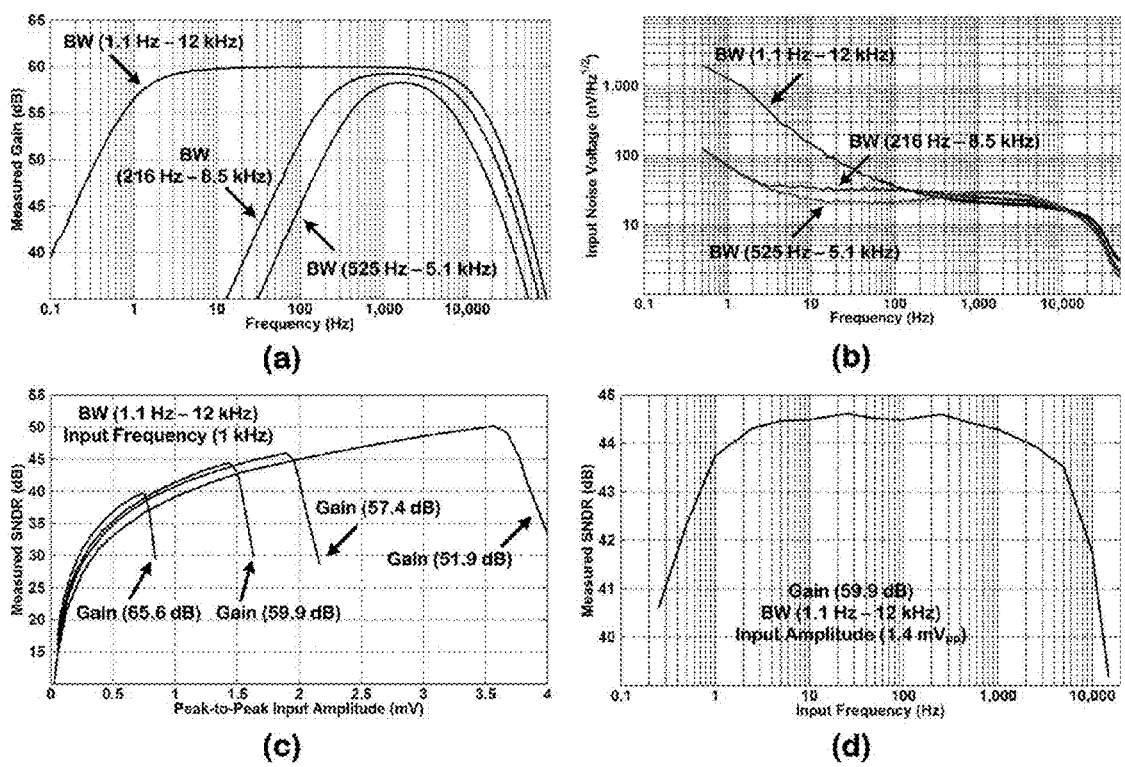

FIGS. 6A-6B are graphs depicting (a) frequency response and (b) input noise voltage of an analog recording front-end of a neural prosthesis with different bandwidth settings. FIGS. 6C-6D are graphs depicting the measured signal-to-noise and distortion ratio (SNDR) of the entire recording front-end at the successive approximation register analog-to-digital converter (SAR ADC) output versus (c) amplitude and (d) frequency of the input signal.

Figures 7A, 7B, 7C, 7D:
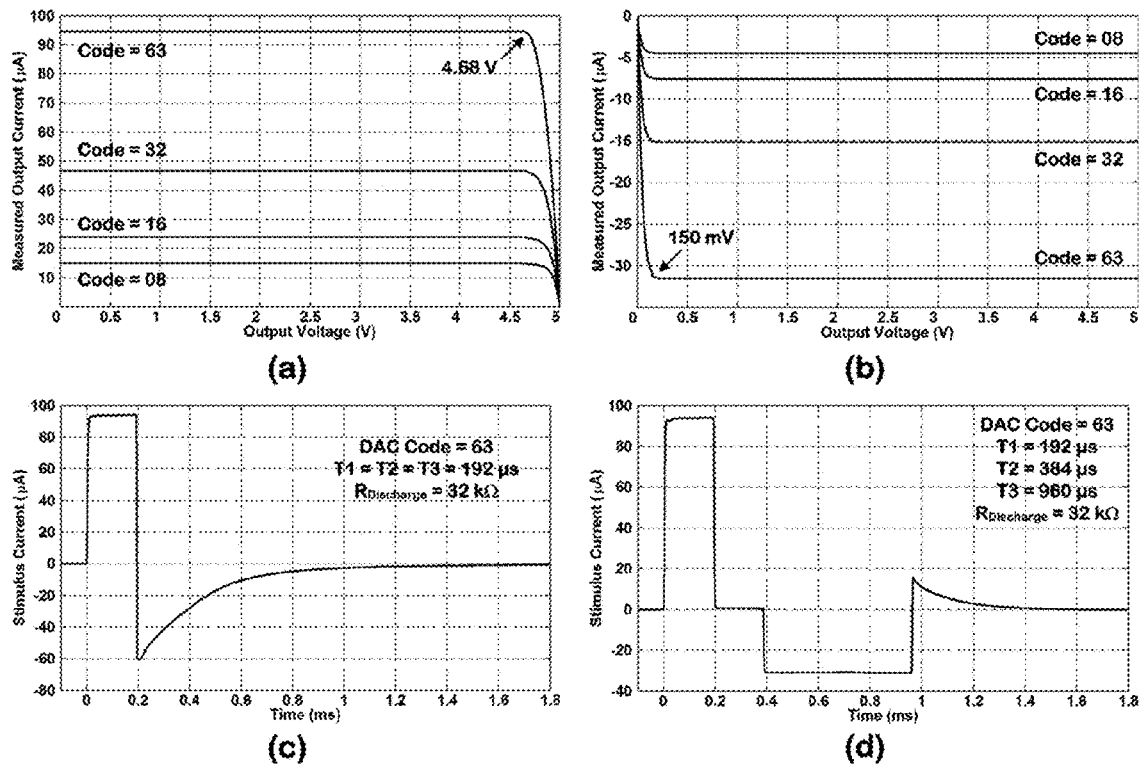

FIGS. 7A-7B are graphs depicting measured microstimulator output current versus output voltage for four different digital-to-analog converter (DAC) input codes in (a) anodic and (b) cathodic phases. FIGS. 7C-7D are graphs depicting measured (c) monophasic and (d) asymmetric biphasic stimulus current waveforms delivered by a neural prosthesis to saline via a microelectrode. Passive discharge is also performed in each case using an on-chip 32-kΩ resistor.

Figure 8:
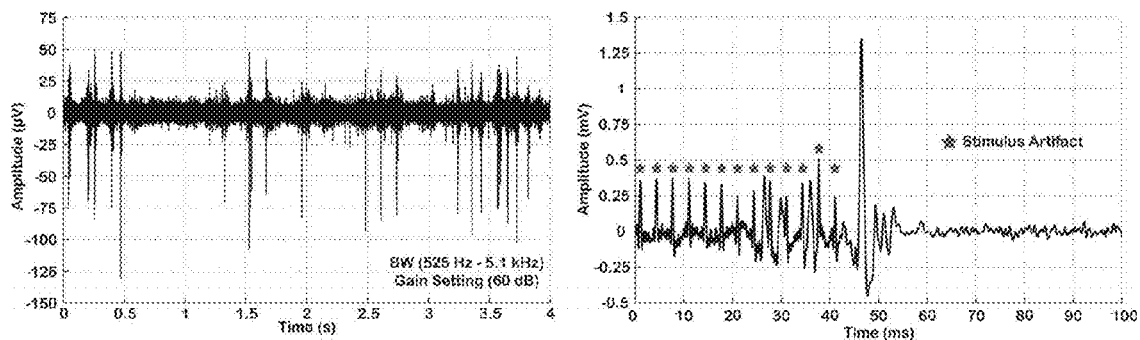

FIG. 8 is an in vivo demonstration of recording and stimulation functionalities of a neural prosthesis in an anesthetized rat. Left—Extracellular neural spikes recorded wirelessly from the somatosensory cortex of the brain. The data are shown after linear-phase offline filtering (500 Hz to 4 kHz) with spike amplitudes referred to the input. Right—Measured electromyogram (EMG) signal from the rat's neck muscle evoked by microstimulation of the cortical motor area with a train of 13 monophasic current pulses. The EMG signal was recorded by commercial electrophysiology equipment.

Figure 9:
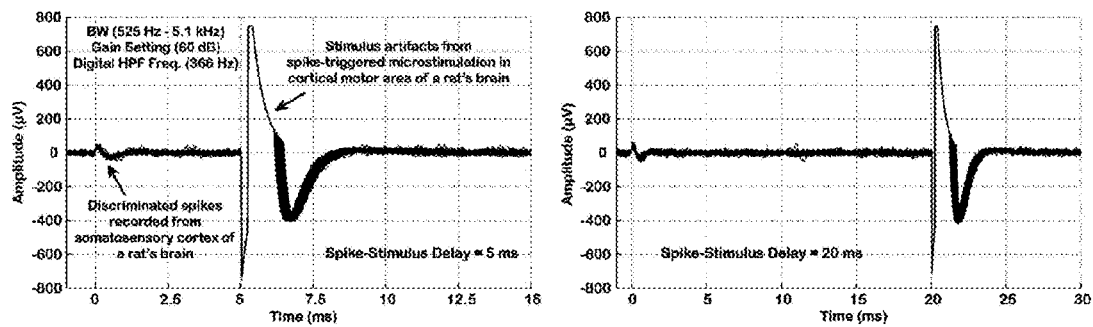

FIG. 9 depicts stimulation on one microelectrode in the cortical motor area of an anesthetized rat triggered by neural spikes discriminated on an adjacent microelectrode in the somatosensory cortex with spike-stimulus delays of 5 and 20 ms. Stimulus artifacts of <4 ms in duration were observed on the recording electrode. The data were recorded wirelessly with the amplitude levels referred to the input.

Figure 10:
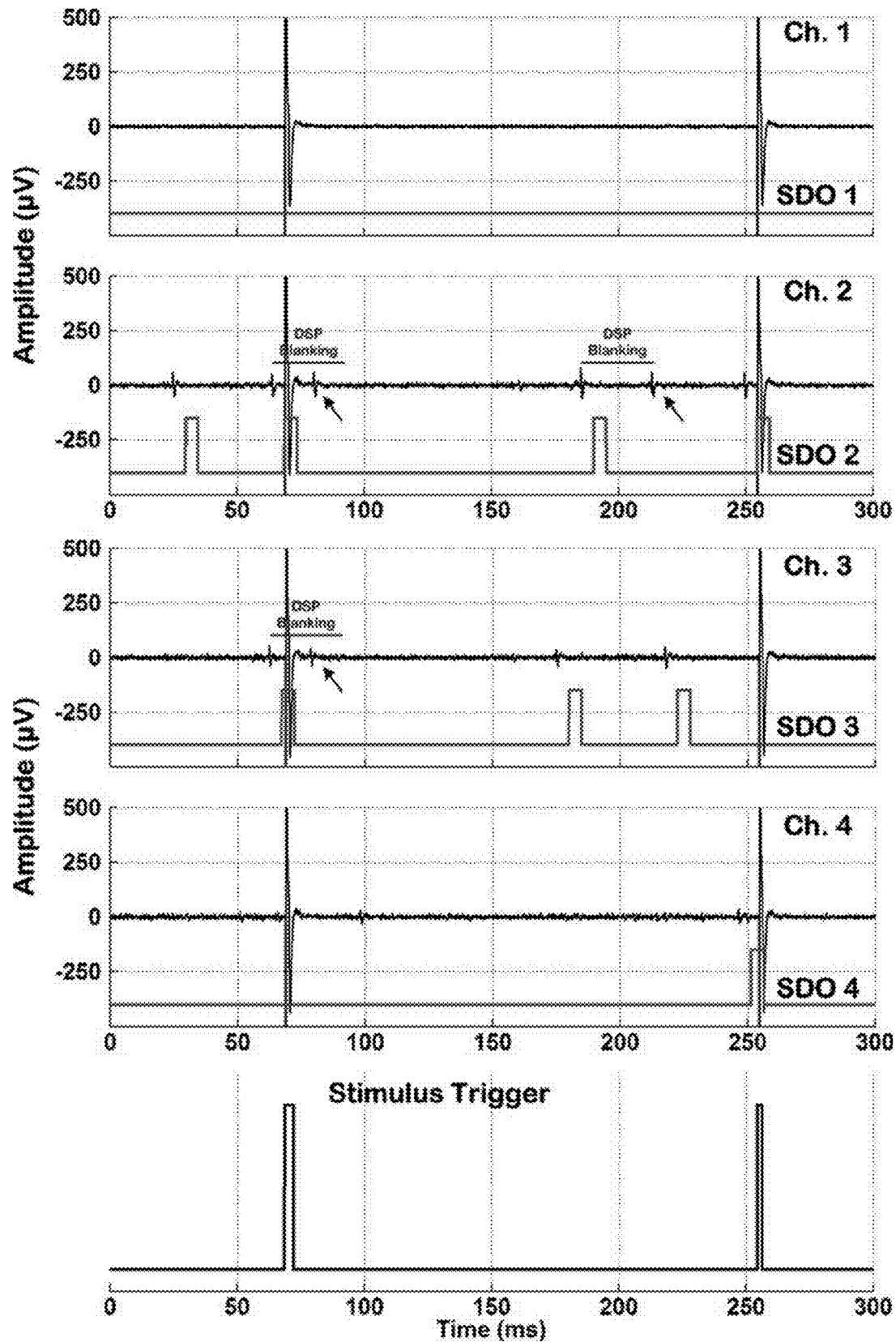

FIG. 10 depicts stimulation on one microelectrode in the cortical motor area of an anesthetized rat triggered by neural spikes discriminated on multiple recording sites of an adjacent microelectrode. The neural prosthesis was programmed to trigger ICMS when neural activity was discriminated on any two or more channels of the recording front-end. The timing parameters $T_5$, $T_6$ and $T_7$ in the DSP unit were set to 5, 10 and 28 ms, respectively. Arrows point to neural spikes on channels 2 and 3 that were not discriminated due to blanking of the DSP operation.

Figure 11:
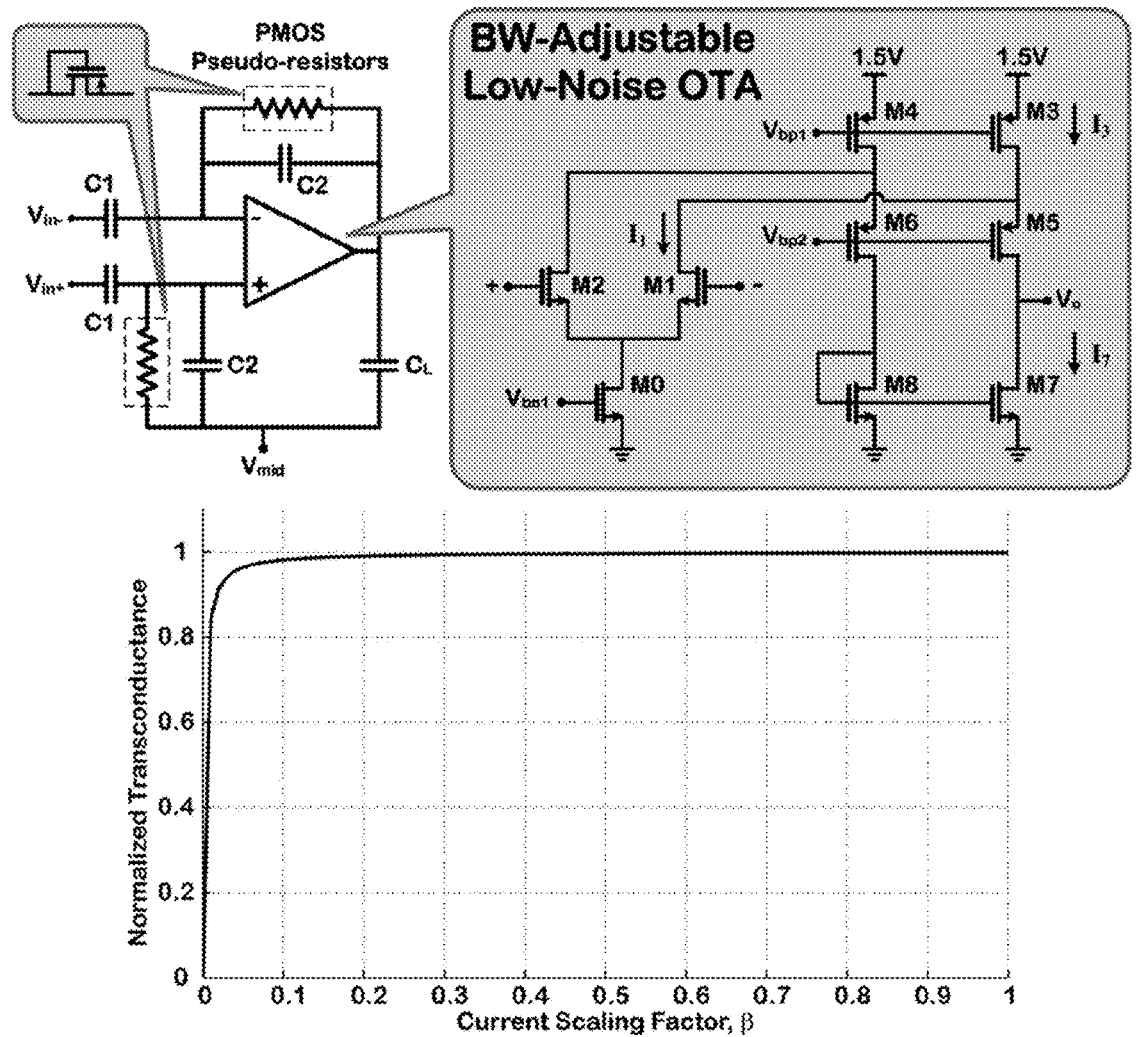

FIG. 11 is a simplified schematic of a low-noise amplifier (LNA) and its core operational transconductance amplifier (OTA) for noise analysis (top) and a plot of the normalized OTA transconductance $G_m/g_{m1}$ versus a scaling factor β (bottom).

Figure 12:
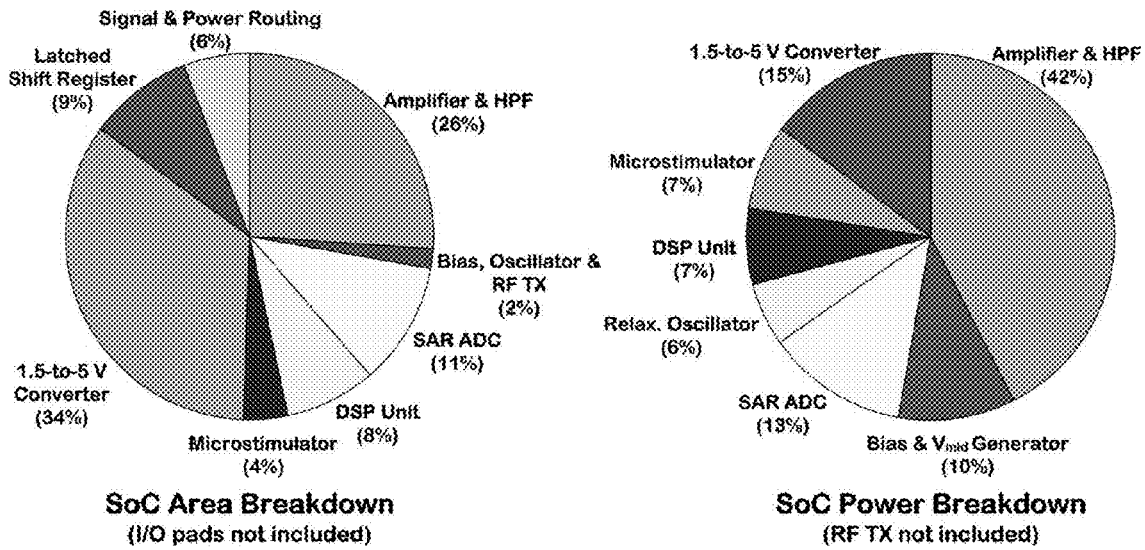

FIG. 12 is a chart depicting a break-down of the area and power consumption for an entire system-on-chip (SoC) of a neural prosthesis suitable for use in the methods of the present disclosure.

Figure 13:
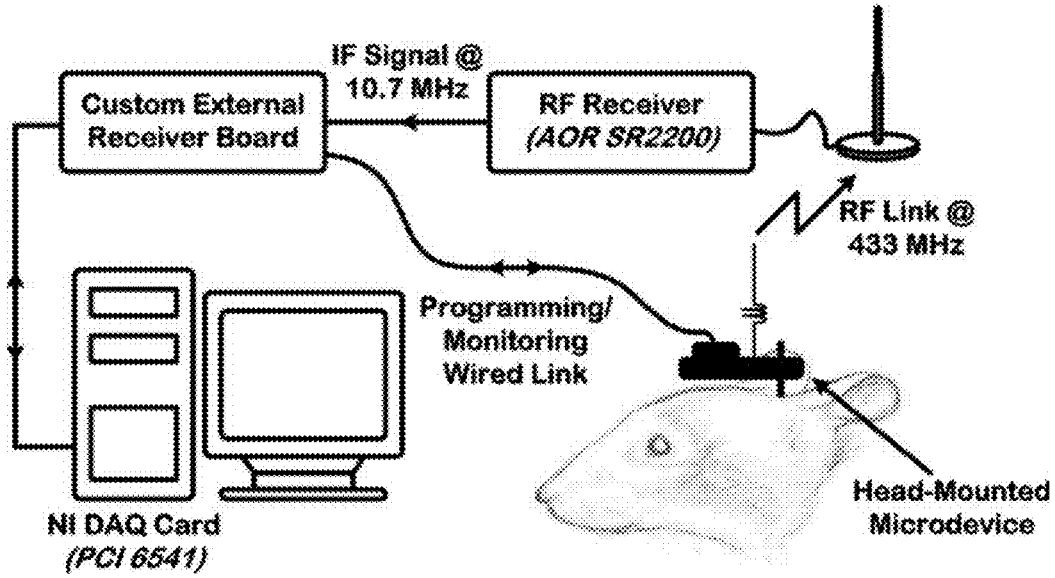

FIG. 13 is an illustration of the experimental setup from Example 2, depicting a head-mounted microdevice for spike-triggered ICMS in an ambulatory rat and peripheral devices for programming and monitoring.

Figure 14:
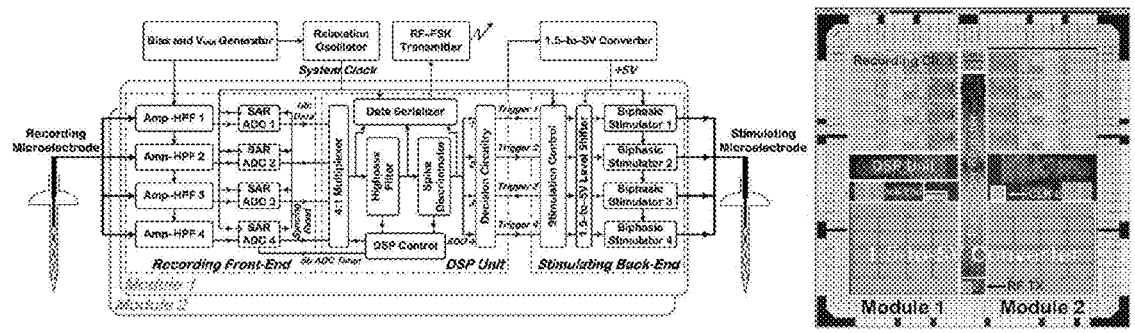

FIG. 14 is a block diagram and a die micrograph of a 3.3 mm×3.3 mm application-specific integrated circuit (ASIC) for spike-triggered ICMS, suitable for use in the methods of the present disclosure.

Figure 15:
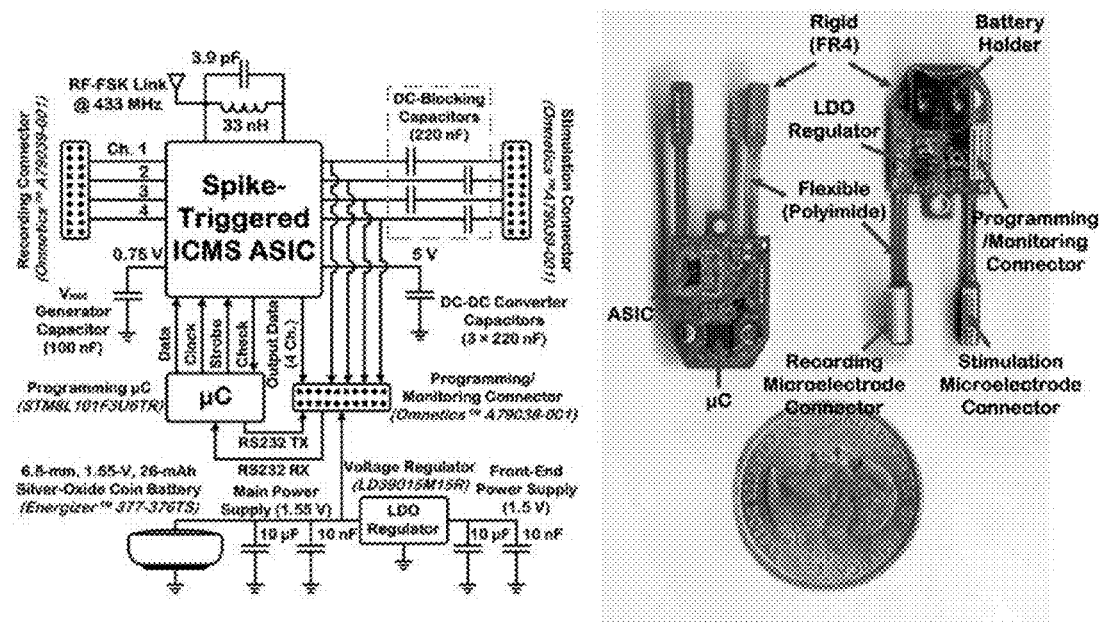

FIG. 15 is a block diagram and a photograph of a fully assembled microdevice suitable for use in the methods of the present disclosure.

Figure 16:
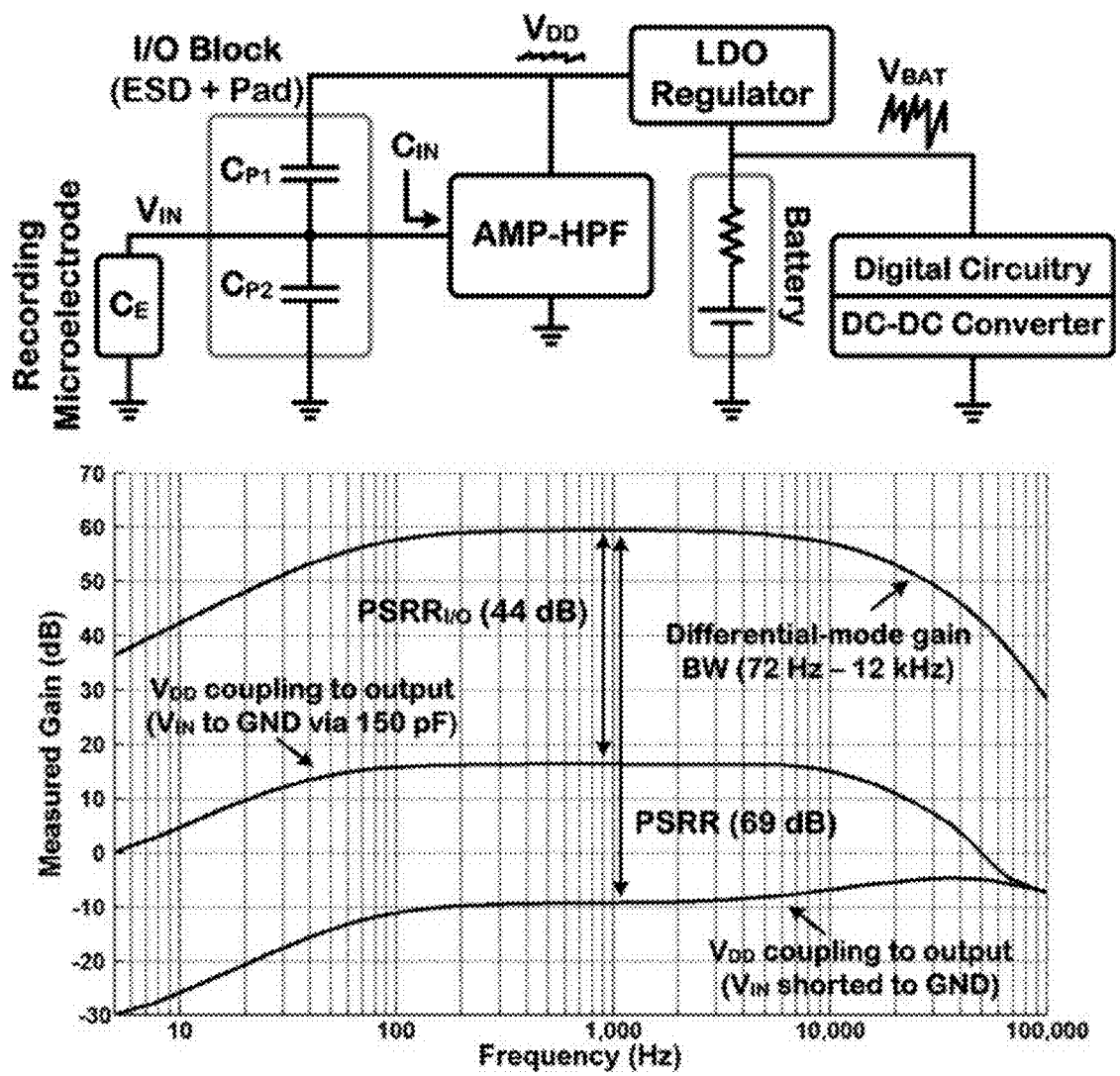

FIG. 16 depicts a mechanism for power supply rejection ratio (PSRR) degradation in an analog recording front-end when interfaced with a recording microelectrode. (Top) Block diagram. (Bottom) Measured PSRR with the input hardwired to ground as well as grounded via a 150-pF external capacitor.

Figure 17:
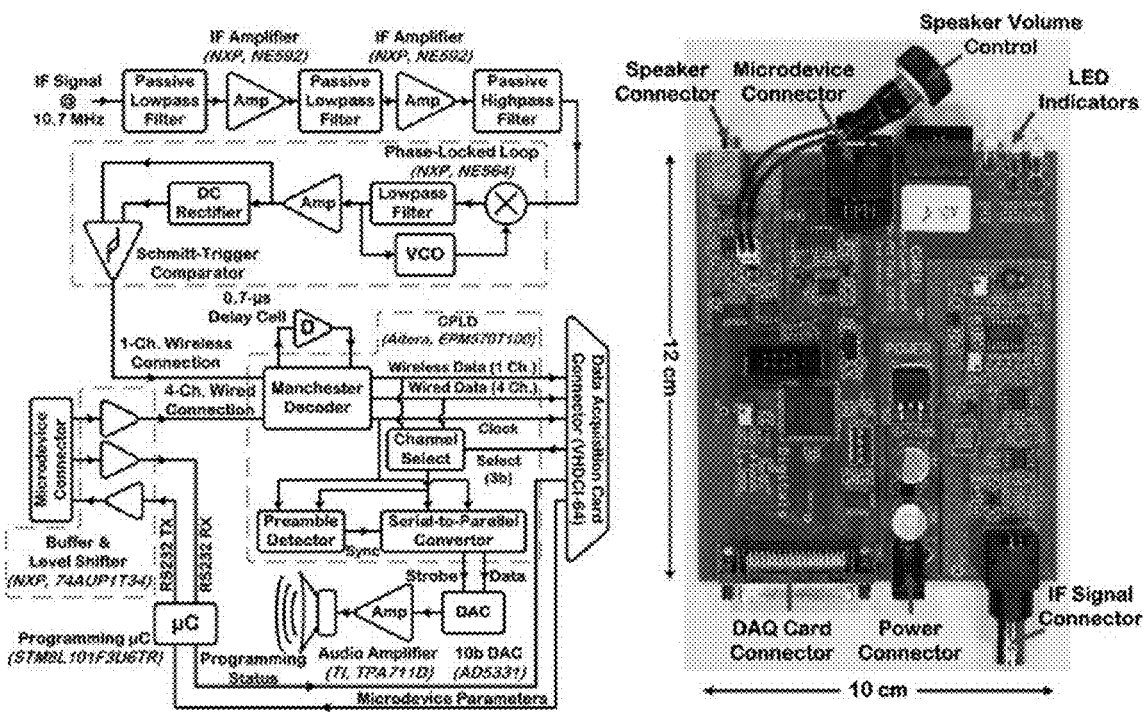

FIG. 17 is a block diagram and a photograph of an external receiver board of a neural prosthesis suitable for use in the methods of the present disclosure.

Figures 18A, 18B, 18C:
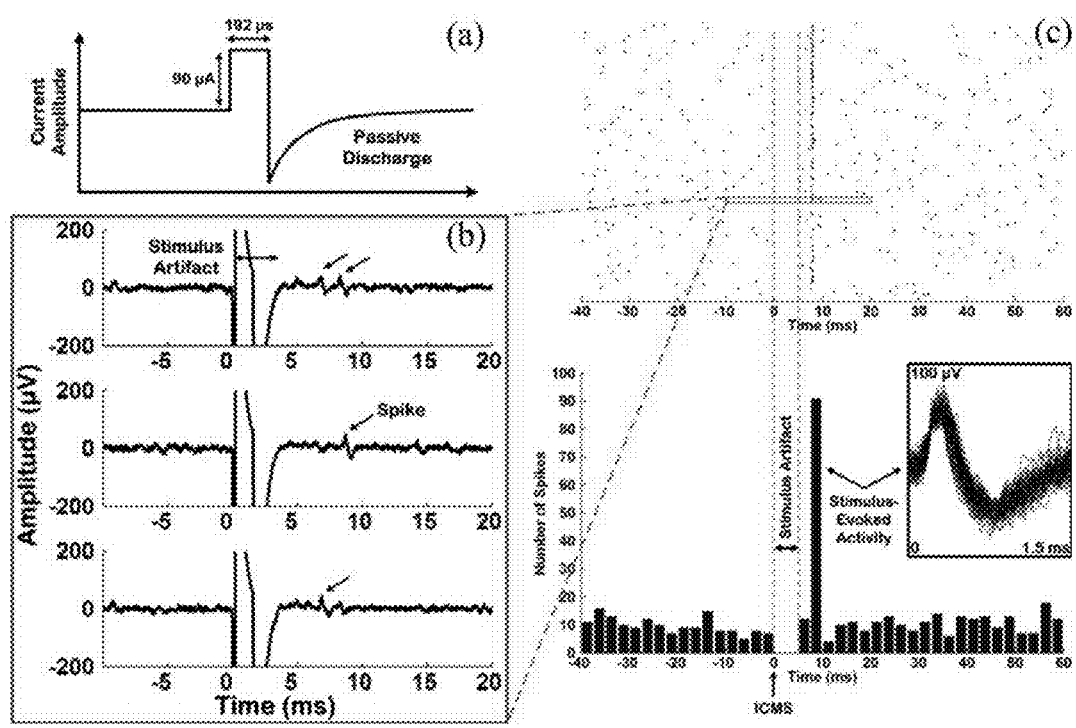

FIGS. 18A-18C depict neural response to ICMS. (a) Monophasic current pulse with passive discharge delivered to the caudal forelimb area (CFA) of a rat's brain at 2 Hz. (b) Traces showing the neural response to ICMS. Arrows indicate spikes detected by the ASIC. (c) Raster plot and peristimulus histogram (2.5-ms bins) of the neural response to ICMS, showing an increase in neural activity after stimulation.

Figure 19:
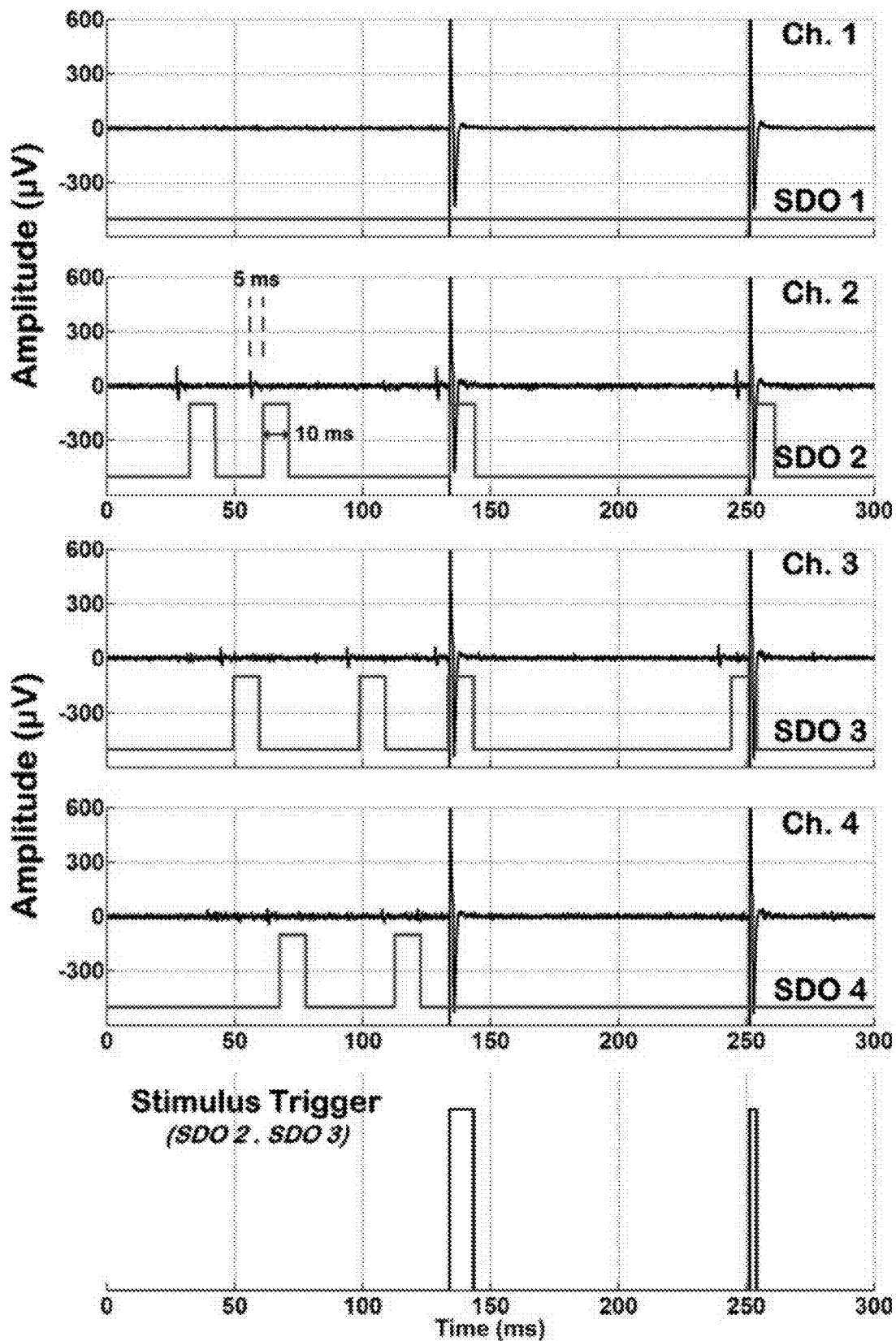

FIG. 19 is a graph showing the simultaneously recorded data on each channel of a multi-channel neural prosthesis at the output of the digital highpass filter (HPF) along with the corresponding spike discriminator output (SDO) and the resulting stimulus trigger signal during a 300-ms time window.

Figure 20:
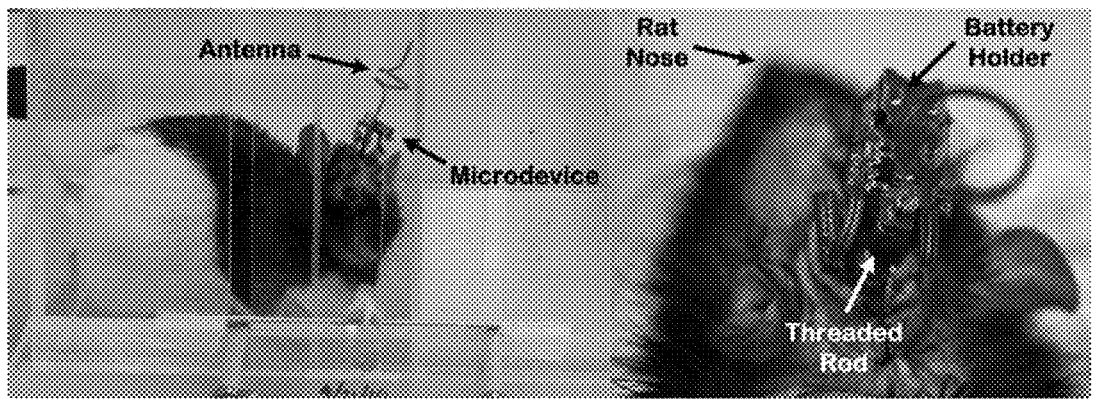

FIG. 20 depicts (Left) ambulatory rat instrumented with a microdevice inside a Plexiglas reaching chamber. (Right) Close-up view of the microdevice on top of the rat's head.

Figure 21:
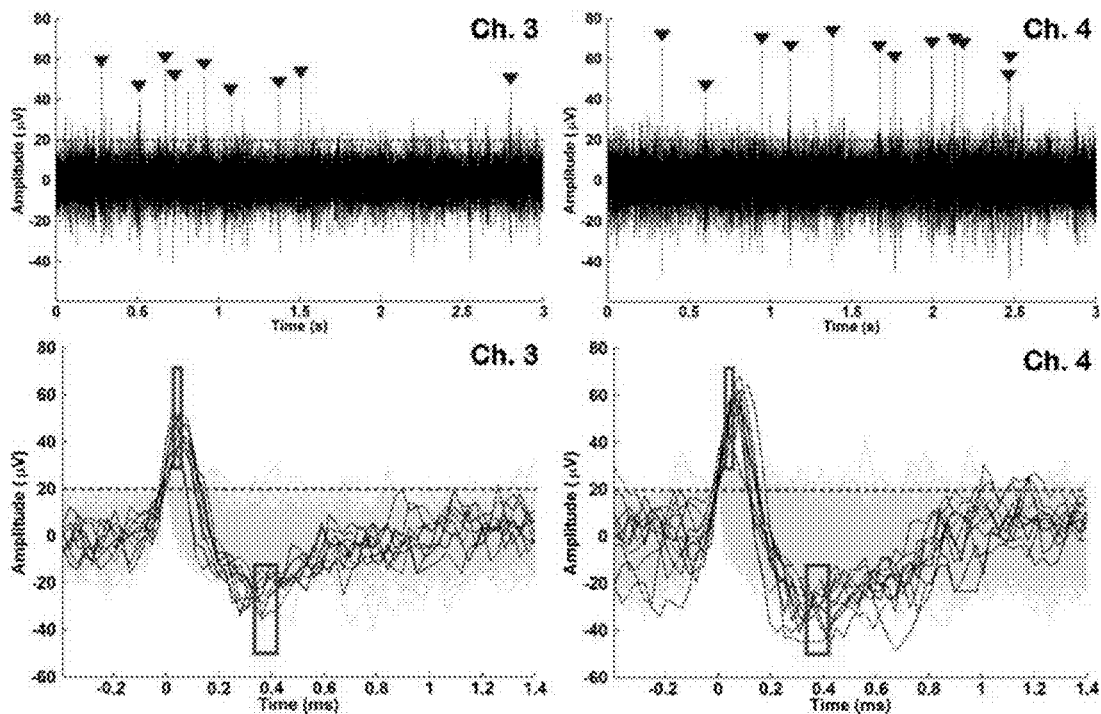

FIG. 21 depicts (Top) 3-s window of neural activity recorded on channels 3 and 4 of the microdevice in an ambulatory rat. (Bottom) Operation of the time-amplitude window discriminator. Spike waveforms in dark gray (and with blue markers in top plot) were accepted for stimulus triggering, whereas those in light gray were rejected by the spike discriminator.

Figure 22:
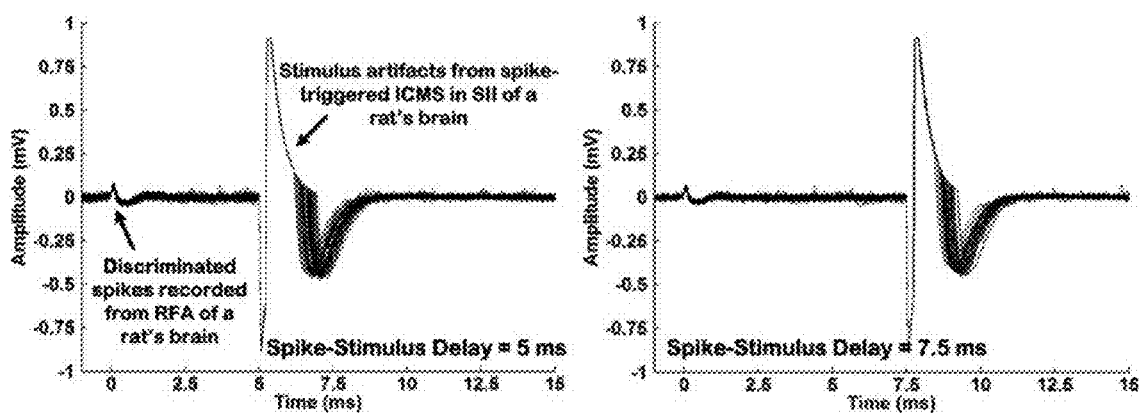

FIG. 22 is a graph showing stimulation on the microelectrode implanted in the second somatosensory area (SII) triggered by neural spikes discriminated on the electrode implanted in the rostral forelimb area (RFA) with spike-stimulus delays of 5 and 7.5 ms. The data were recorded wirelessly with the amplitude levels referred to the input.

Figure 23:
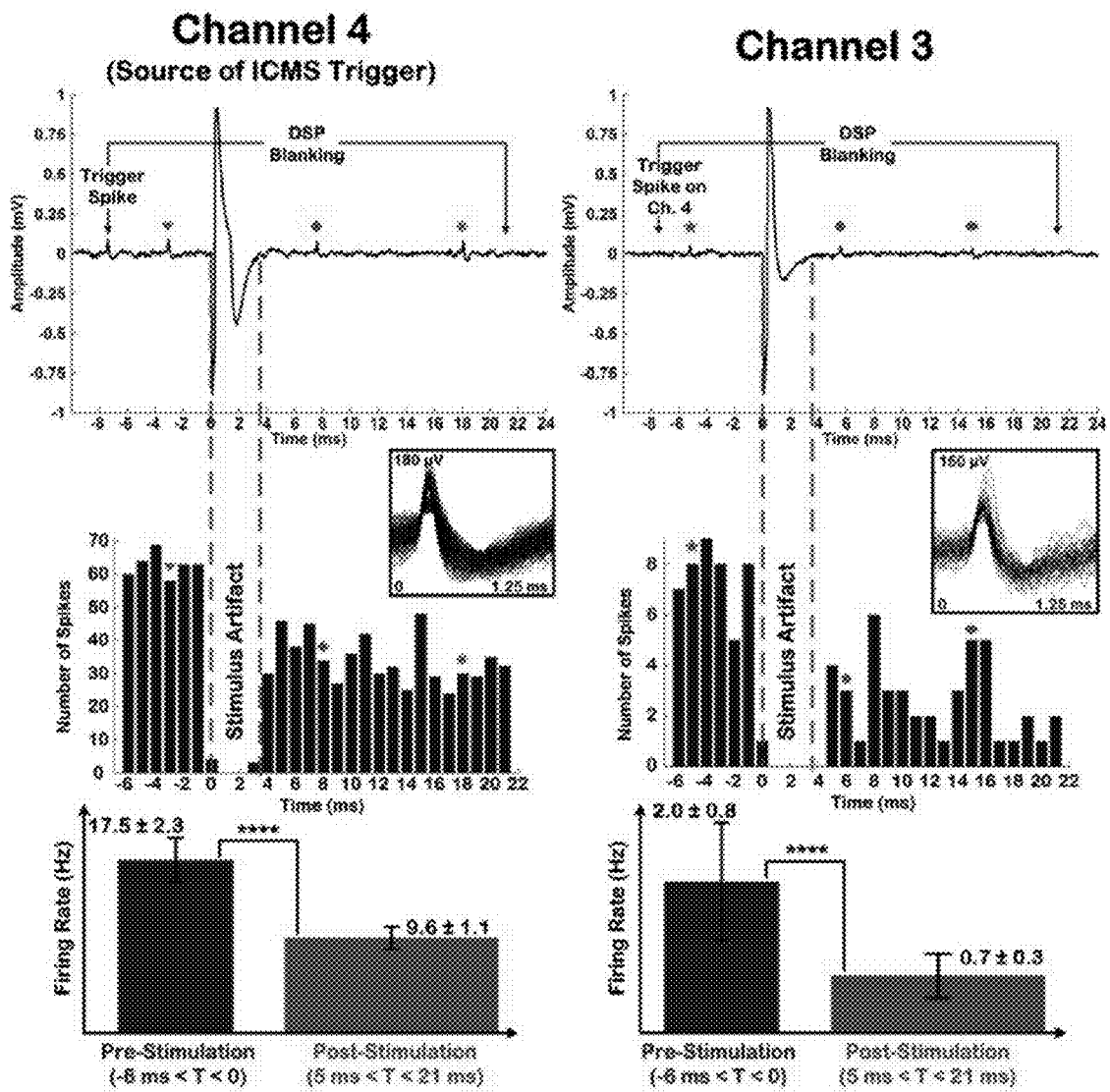

FIG. 23 depicts modulation of the neuronal firing rate due to ICMS triggered by neural spikes discriminated on one channel of a multi-channel neural prosthesis. (Top) 34-ms window of recorded data on channels 3 and 4, showing a stimulus artifact and neural spikes. (Middle) Peristimulus histogram of neural activity (1-ms bins) during DSP blanking period. (Bottom) Mean neuronal firing rate pre- and post-stimulation. Paired T-test showed the reduction in firing rate was statistically significant with $p<0.0001$. Insets depict the time-aligned and superimposed neural spikes in each histogram, except for those at t=0 (4 spikes on channel 4 and 1 spike on channel 3). The data were recorded via a wired link.

Figure 24:
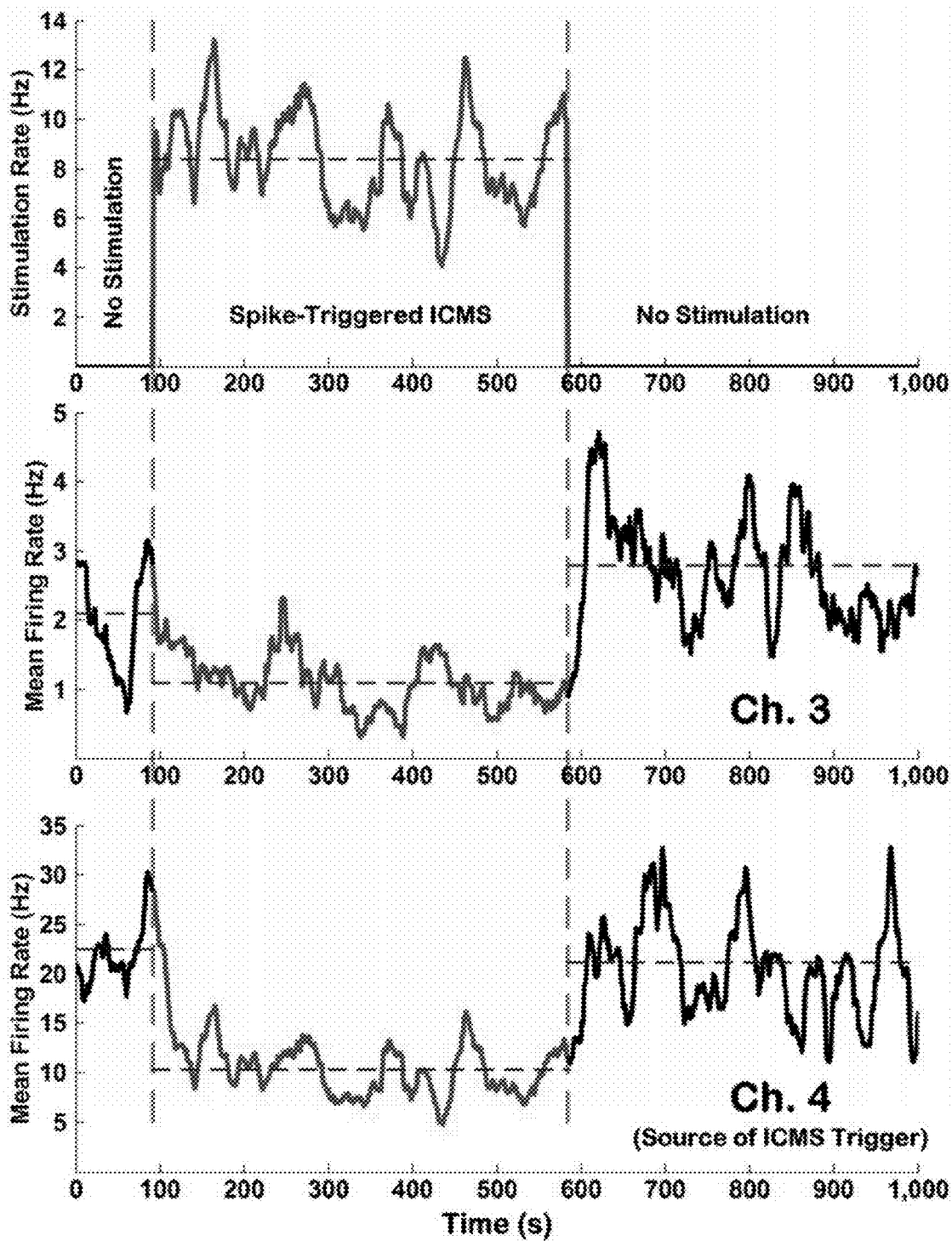

FIG. 24 depicts the modulation of neuronal firing rate due to ICMS triggered by neural spikes discriminated on one channel of a multi-channel neural prosthesis over a much longer time scale.

Figure 25A:
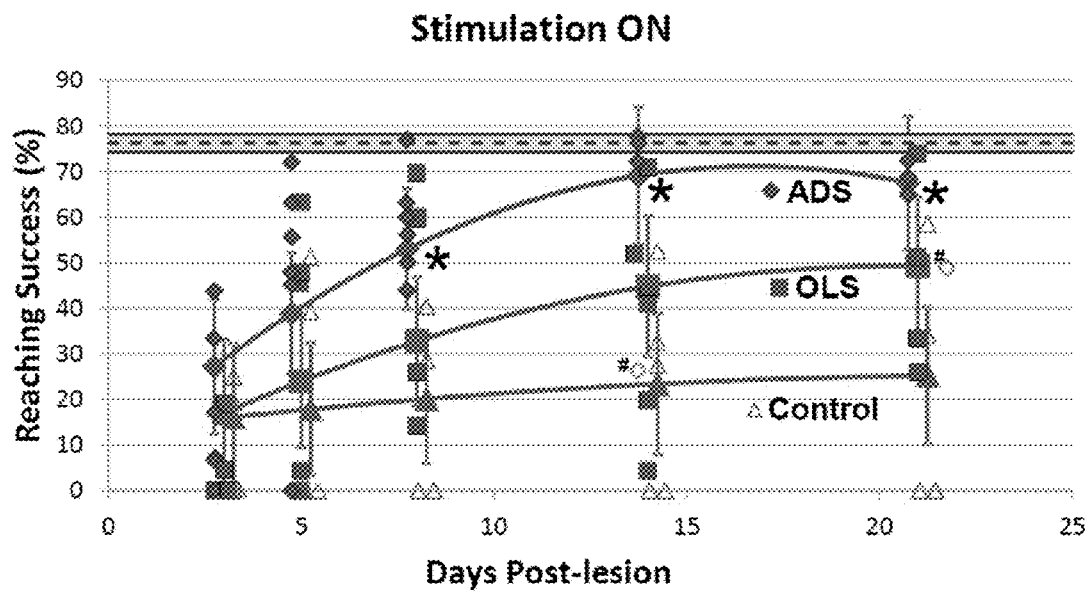
Figure 25B:
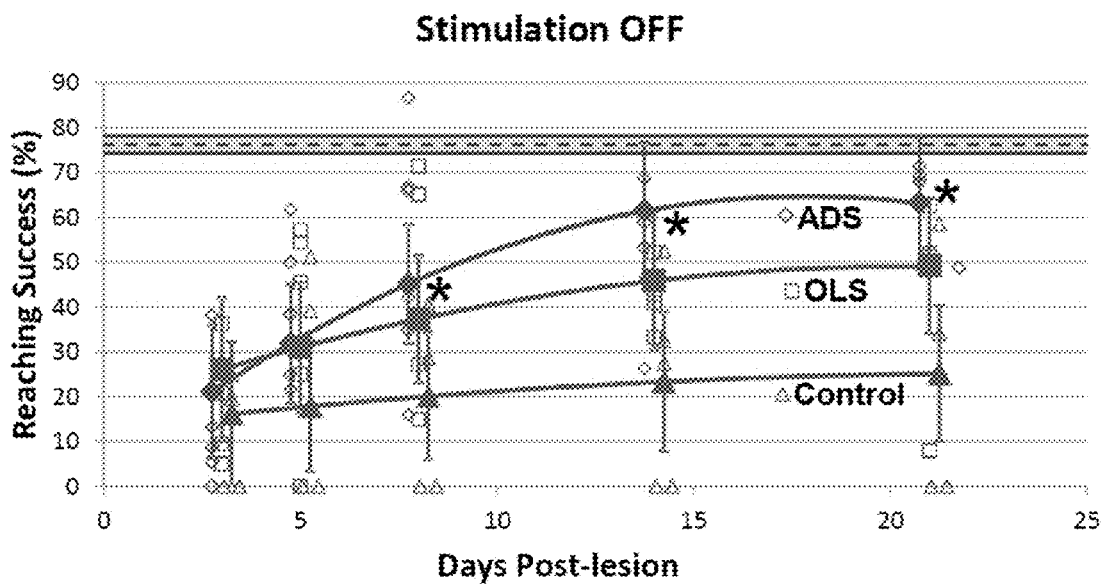

FIGS. 25A-25B show a comparison of the success rate on the reaching task across groups after brain injury. Prior to brain injury (Day 0), all animals were required to reach a 70% baseline success rate on the reaching task. Dotted line indicates average pre-injury performance of all animals in the study. Shaded area indicates the 95% confidence interval. Following cortical impact, the microdevice was programmed to deliver appropriate stimulation. On behavioral testing days 3, 5, 8, 14 and 21, animals did 20 trials with the stimulation on (A) and 20 trials with the stimulation off (B). Regression lines are based on a linear mixed model. Individual data points are also superimposed on each graph. A) Comparison of reaching success between activity-dependent stimulation (ADS; red), randomized open-loop stimulation (OLS; green) and control (blue) animal groups when the stimulation was turned on during the trial (except in control group, which received no stimulation): B) Comparison between the three groups when the stimulation was turned off during the session. Reaching success was significantly better in the ADS group compared to the other groups on post-injury days 8, 14, and 21 in both the on and off states. In this and the following figure, error bars represent standard error of the mean. *$p<0.05$ (difference between ADS group and both OLS and control groups). # Device not functioning.

Figure 26:
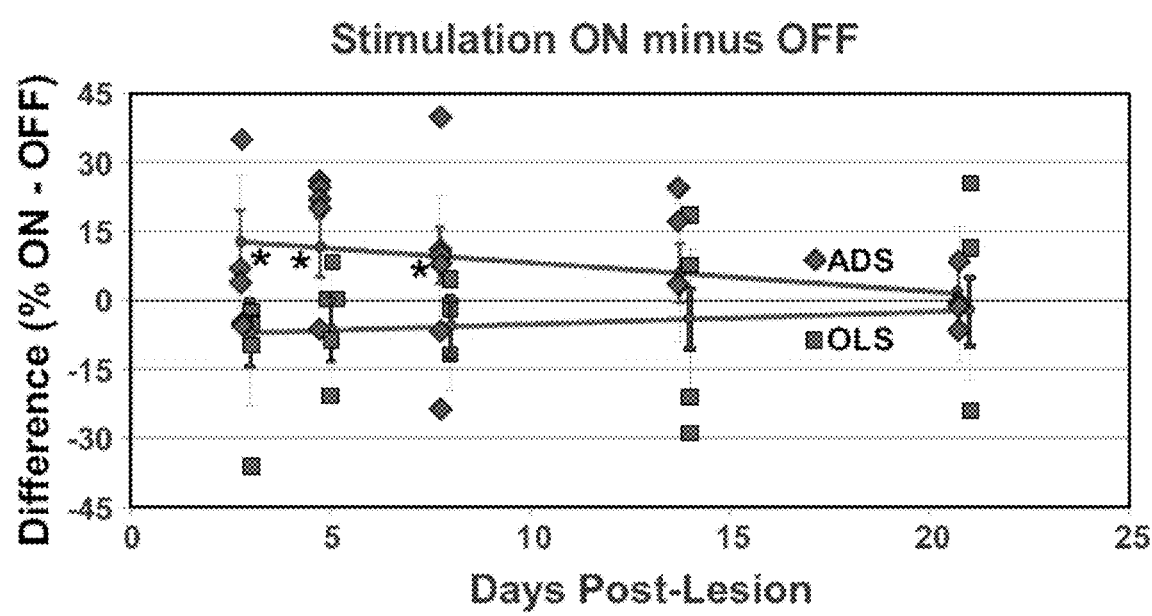

FIG. 26 shows a comparison of the success rate on the reaching task within groups contrasting on and off stimulation states. On each of post-injury days 3, 5, 8, 14 and 21, reaching success with stimulation off was subtracted from reaching success with stimulation on. Activity-dependent stimulation (ADS) group is shown in red and open-loop stimulation (OLS) group is shown in green. On post-injury days 3, 5, 8 and 14, reaching success in the ADS group, but not the OLS group, was superior with stimulation on compared with stimulation off. *p<0.05 (difference between ADS and OLS groups).

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to methods and associated neural prosthetic devices (i.e., microdevices) for bridging brain areas for the purpose of restoring or improving neurological function. More particularly, the present disclosure relates to, in one embodiment, multi-channel neural prosthetic devices and, in other embodiments, methods for utilizing a neural prosthetic device to function as a bridge between two neural sites between which there is substantially no effective communication.

Methods

In one embodiment, a method of the present disclosure comprises detecting a neural spike in a first neural site in a subject and delivering a stimulus to a second neural site in the subject within a defined period of time after the detection of the neural spike, wherein there is substantially no effective communication between the first and second neural sites. In some embodiments, the detection of a neural spike and the corresponding delivery of a stimulus may be repeated continuously. As used herein, "effective communication" refers to temporally correlated activity between neurons that is necessary for normal behavioral function. Effective communication can either occur due to direct, physical connections between the neurons, or indirect connections via intermediate neural structures.

As would be recognized by one of ordinary skill in the art, the absence of effective communication between two or more neural sites may be generally known based on, for example, available literature, and experiments (e.g., tract-tracing, neurophysiology or neuroimaging (such as, e.g., diffusion-tensor imaging and resting-state connectivity)), or by utilizing any other method known to one of ordinary skill in the art for determining the absence of effective communication.

In one embodiment, the methods of the present disclosure may allow a neural prosthetic device to act as a communication bridge between two or more neural sites, including sites in different regions of the brain. In some embodiments, the neural sites may have substantially no effective communication. Suitable neural sites can be located in any region of the brain such as, for example, in a cortical region of the brain (e.g., in motor cortex, sensory cortex, frontal cortex, occipital cortex, temporal cortex or parietal cortex), corpus callosum, subcortical areas (e.g., thalamus, hypothalamus, limbic system, basal ganglia, amygdala, hippocampus), cerebellum, and olfactory bulb and/or tract. Further neural sites may be located in the spinal cord. Suitable sites outside of the brain and spinal cord include muscles. Accordingly, when used in subjects that have a cortical or subcortical communication disruption, which may be caused by an injury resulting from a stroke, a traumatic brain injury (TBI), a neurosurgical resection, a tumor, epilepsy, a spinal cord injury, etc., the methods of the present disclosure may provide the subject with functional recovery in the affected area. Such functional recovery may include, but is not limited to, improved speech, language comprehension, executive function, attention, memory, learning abilities, motor abilities and sensory abilities, as well as reduction in symptoms such as neglect, depression, spasticity, tremor, etc. In some embodiments, the methods of the present disclosure may serve to reduce symptoms of psychiatric disorders and autism spectrum disorders such as nonverbal communication skills, abnormal sensory perceptions, etc. In some embodiments, the methods of the present disclosure may serve to improve function in various types of disconnection syndromes, such as white matter dementia, conduction aphasia, disorders of consciousness, developmental dyslexia, tactile aphasia, etc. In some embodiments, the methods of the present disclosure may serve to improve function in certain types of disconnection syndromes beyond those involving a focal injury, such as Parkinson's disease. In some embodiments, the methods of the present disclosure may also serve as a guidance cue for regenerating or sprouting nerve fibers.

In some embodiments, the methods of the present disclosure also provide for a neural communication bridge in cortex or subcortical structures to alleviate functional disorders in idiopathic conditions, i.e., when specific dysfunctional communication cannot be identified. In some embodiments, the methods of the present disclosure also provide a neural communication bridge in cortex or subcortical structures to improve function or behavioral performance in otherwise healthy brains. Such methods may be implemented using a neural prosthetic device of the present disclosure.

Neural prosthetic devices suitable for use in the methods of the present disclosure will be further discussed in more detail below; however, such devices generally comprise an integrated circuit that comprises a recording front-end comprising one or more recording channels, a processor unit, and a stimulus delivering back-end comprising one or more stimulation channels.

In one embodiment, a neural spike in a first neural site may be recorded using a recording electrode that may be implanted in a subject at the first neural site and externally interfaced with one or more recording channels of a recording front-end of a neural prosthetic device. As would be recognized by one of ordinary skill in the art with the benefit of this disclosure, multi-site recording electrodes may be utilized in conjunction with a multi-channel neural prosthetic device so as to detect neural signals from a plurality of neural sites. Examples of suitable recording electrodes may include, but are not limited to, microelectrodes comprising silicon or tungsten with recording sites of iridium. Similarly, a recording electrode may be externally interfaced with a recording front-end of a neural prosthetic device in any suitable manner, which may be temporary or permanent. In some embodiments, it may be desirable to interface a recording electrode with a recording front-end of a neural prosthetic device via a microconnector in a plug-and-play fashion so as to allow for disconnection in the event that the neural prosthetic device needs to be replaced or is no longer needed.

After a neural spike is recorded, it is transmitted to a processor unit comprising a spike discriminator that identifies whether the neural spike is acceptable as a stimulus trigger signal for a stimulus delivering back-end. In some embodiments, a spike discriminator identifies acceptable neural spikes by using a spike discrimination algorithm, which may utilize adjustable, user-set parameters. While one of ordinary skill in the art with the benefit of this disclosure would be able to determine suitable parameters, such exemplary parameters may consist of a threshold level and a time-amplitude window. Using this example, an acceptable neural spike would be one that crosses the threshold level and passes through the time-amplitude window. Furthermore, in certain embodiments, the multichannel recording capabilities add another level of rejection. Even if spike events are accepted based on the preceding criteria, they may represent random neuronal activity that is not closely related to the function of interest. By requiring the preceding criteria to be met on multiple recording channels, the user can further restrict triggering. This is accomplished by a decision-making algorithm in the DSP unit. User-set parameters can be adjusted to define the time window within which the multiple spike events occur.

In some embodiments, it may be advantageous to adjust user-set parameters to reduce or prevent false-triggering caused, at least in part, by stimulus artifacts. After an acceptable neural spike is detected and the stimulus delivering back-end stimulates a neural site, an artifact from the stimulation may falsely trigger a neural prosthetic device and initiate a second stimulation cycle. In an effort to avoid this, user-set parameters in the form of a threshold level and time-amplitude window in the processor unit may be adjusted to discriminate between stimulus artifacts and neural spikes. Additionally, blanking the processor unit operation after spike discrimination also prevents false-triggering.

If a neural spike, or a combination of neural spikes, is accepted as a stimulus trigger signal, then the stimulus delivering back-end will deliver a stimulus to a second neural site, or to a plurality of neural sites. Accordingly, a stimulus may be delivered to a second neural site using a stimulating electrode, which may be implanted in a subject at the second neural site and externally interfaced with one or more stimulation channels of a stimulus delivering back-end of a neural prosthetic device. Multi-site stimulation electrodes may be utilized in conjunction with a multi-channel neural prosthetic device so as to deliver a stimulus to a plurality of neural sites. As mentioned above with respect to recording electrodes, examples of suitable stimulation electrodes may include, but are not limited to, microelectrodes comprising silicon or tungsten with stimulation sites of iridium oxide. Similarly, a stimulation electrode may be externally interfaced with a stimulus delivering back-end of a neural prosthetic device in any suitable manner, which may be temporary or permanent. In some embodiments, it may be desirable to interface a stimulation electrode with a stimulus delivering back-end of a neural prosthetic device via a microconnector in a plug-and-play fashion so as to allow for disconnection in the event that the neural prosthetic device needs to be replaced or is no longer needed. A recording electrode may likewise be interfaced with a recording front-end of a neural prosthetic device via a microconnector in a plug-and-play fashion. Furthermore, a flexible interconnect for interfacing an electrode with either the recording front end or the stimulus delivering back-end of a neural prosthetic device may be used in order to allow for some adjustability in microelectrode placement during implantation, simplifying the surgical procedure.

In some embodiments, the stimulation channel or channels of a stimulating back-end of a neural prosthetic device may comprise current-blocking capacitors to prevent any net dc current flow into the tissue contacted by a stimulation electrode, potentially arising from semiconductor failure or charge imbalance.

In some embodiments, it may be particularly advantageous to adjust the period of time between spike discrimination and stimulus onset. Such adjustability allows for patient-specific operation for optimized performance. For example, in some embodiments, the time period between which a neural spike is detected and a stimulus is subsequently delivered may be <1000 ms (e.g., <800 ms, <500 ms, <200 ms, <30 ms). In other embodiments, the time period may be reduced further, so as to achieve as little time lag as possible between a recorded spike and a stimulus (e.g., <20 ms, <10 ms, or <5 ms). In some embodiments, the particular period of time between spike discrimination and stimulus onset may be adjusted to replicate the normal timing relationships between the areas, which may depend on, among other things, distance, fiber size (e.g., larger fibers conduct at higher velocity), whether interconnecting fibers are myelinated (e.g., faster conduction velocity in myelinated fibers).

In certain embodiments, the stimulus delivered may be an electric stimulus that may be monophasic or biphasic. In some embodiments, the stimulation may have an intensity of ≤10 mA (e.g., ≤5 mA, ≤1 mA, ≤500 µA, ≤300 µA, ≤100 µA) and duration of about 1 ms (e.g., 200 µs). Typically, current levels may range from 1 µA to 10 mA, depending largely upon electrode characteristics, and pulse duration may range from 50 µs to 1 ms (e.g., 200 µs). In certain embodiments, a train of pulses may be delivered per each trigger, ranging from 1 to 200 pulses.

In some embodiments, the method of spike recording and stimulus delivery may be repeated for a set amount of time such that a new communication link or links between two or more neural sites are established during performance of the method, after, or both. For example, the method may be performed for a period of 14 days, during which time a neural prosthetic device creates an artificial bridge between two or more neural sites, and after which time communication continues between the two or more neural sites, wherein there previously had existed substantially no effective communication between the two or more neural sites. The method may also be performed for a shorter or longer period of time (e.g., 8 days, 5 days, 30 days, or 60 days).

Neural Prosthetic Devices

In one embodiment, the methods of the present disclosure may be performed utilizing any neural prosthetic device capable of detecting a neural spike in a first neural site and delivering a stimulus to a second neural site within a defined period of time after detection. Examples of suitable neural prosthetic devices that may be utilized in the methods of the present disclosure include, but are not limited to, those devices disclosed in U.S. Patent Application Nos. 2009/0105786, 2007/0032738, 2006/0173259, 2005/0240242, 2005/0119703, 2006/0009814, 2007/0032834, 2007/0179584, 2007/0112393, and 2006/0200206.

Figure 1:
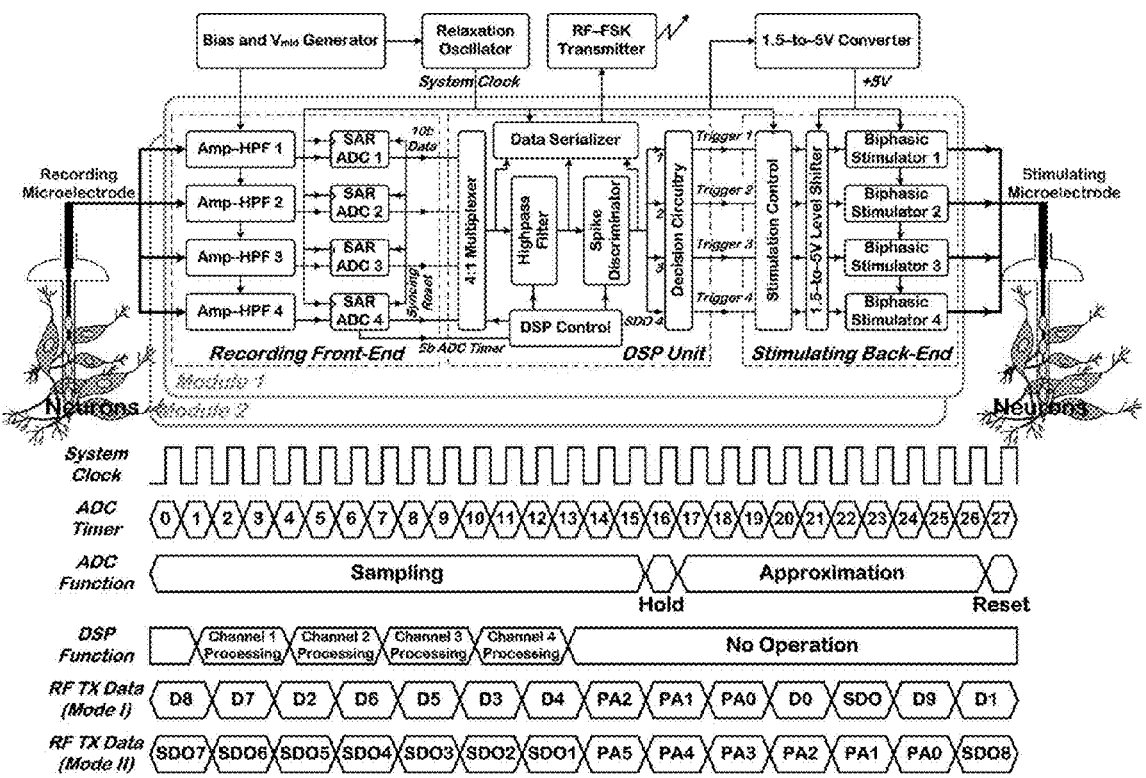
FIG. 1 depicts the proposed architecture and timing operation of a neural prosthesis for activity-dependent intracortical microstimulation (ICMS), suitable for use in the methods of the present disclosure. There are two identical 4-channel modules per chip powered by a single 1.5-V battery.

In another embodiment, the present disclosure provides a neural prosthetic device, which may be utilized in the methods described above, comprising an integrated circuit that comprises a recording front-end comprising a plurality of recording channels; a processor unit; and a stimulus delivering back-end comprising a plurality of stimulation channels. The circuit is characterized as having a recording front-end that is operably connected to a stimulus delivering back-end such that a relevant recording of one or more neural spikes by the front-end can induce one or more relevant stimulations by the back-end. FIG. 1 depicts a specific exemplary embodiment of a neural prosthetic device of the present disclosure. Additionally, examples 1-3 below describe a specific embodiment of a neural prosthetic device comprising an integrated circuit that comprises a recording front-end comprising a plurality of recording channels, a processor unit, and a stimulus delivering back-end comprising a plurality of stimulation channels.

Figure 2:
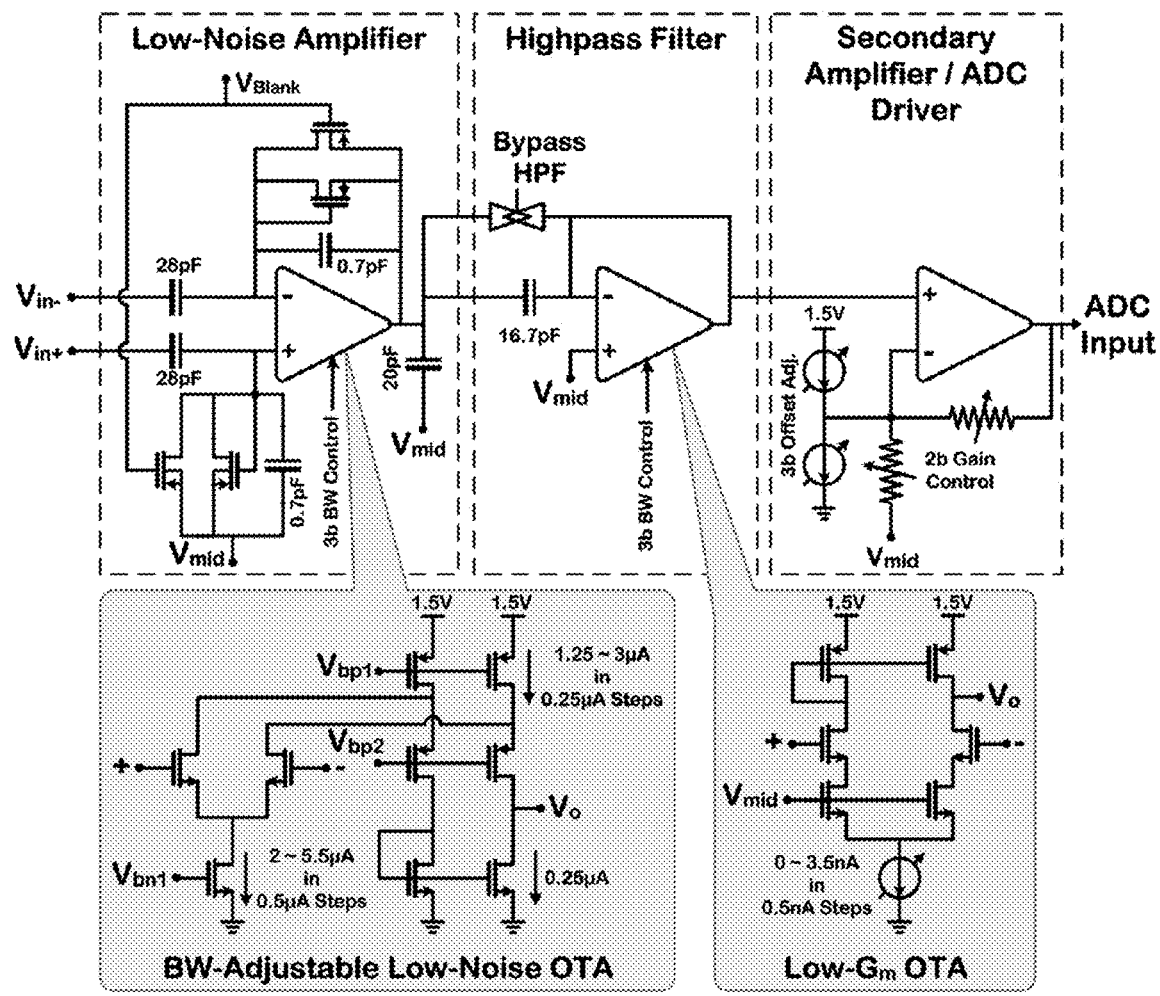
FIG. 2 is a circuit schematic of the analog recording front-end of one channel in a neural prosthesis suitable for use in the methods of the present disclosure.

In some embodiments, a recording front-end of a neural prosthetic device of the present disclosure provides ac amplification, dc input stabilization, bandpass filtering and digitization to the recorded neural signals with fully programmable gain and bandwidth. Accordingly, in some embodiments, a recording front-end may comprise a low-noise amplifier (LNA), a highpass filter (HPF), a secondary amplifier and an analog-to-digital converter (ADC), specific examples of which are further discussed in the examples below. FIG. 2 depicts an exemplary circuit schematic of a recording front-end of a neural prosthetic device that includes a low-noise amplifier, a highpass filter, and a secondary amplifier, which also serves as an ADC driver. The ADC then converts the amplified neural signal into digitized form for further processing by the monolithic digital signal processing unit.

In some embodiments, a processing unit of a neural prosthetic device of the present disclosure may be a digital signal processing unit. In some embodiments, a digital signal processing unit suitable for use in the present disclosure may comprise a multiplexer, one or more filters (such as digital highpass filters), a spike discriminator, and decision circuitry used to generate a stimulus trigger signal. A multiplexer may allow for a multi-channel device to share the same processing unit. Upon determining that a neural spike is accepted as a stimulus trigger signal, a spike discriminator may send a stimulus trigger signal to a stimulus delivering back-end. FIG. 3 depicts an exemplary digital signal processing unit comprising a spike discriminator.

In some embodiments, a stimulus delivering back-end of a neural prosthetic device of the present disclosure may comprise, in addition to a plurality of stimulation channels, a stimulator timing control, a signal level shifter, and a digital-to-analog converter. As mentioned above, in some embodiments, the stimulus delivering back-end may have a user-adjustable time delay so as to deliver a stimulus at the desired period of time after neural spike discrimination. FIG. 4 depicts an exemplary circuit schematic of a stimulus delivering back-end of a neural prosthetic device.

In some embodiments, a neural prosthetic device of the present disclosure may also comprise a radio-frequency (RF) transmitter and a battery. In those embodiments where the neural prosthetic device comprises an RF transmitter, it may be used to transmit data to an external RF receiver. The data may consist of the neural signals and neural spikes on the multiple channels. Before transmitting the relevant data, a data serializer may be used to convert the recorded or processed data on each of the channels into a serialization format that can be stored and transmitted. Additionally, a neural prosthetic device of the present disclosure may also be powered by a battery.

In certain embodiments, the present disclosure also provides a system for monitoring and programming a neural prosthetic device as described herein. The system may comprise a link for transmitting neural spikes and device data, an external receiver board that processes the transmitted data and receives and uses parameter data from a personal computer (PC) for programming a neural prosthetic device, a digital data acquisition (DAQ) card that establishes a connection between the external receiver board and a PC, a PC that stores the processed data and uses software to monitor and determine parameter data for programming a neuroprosthetic device.

To facilitate a better understanding of the present disclosure, the following examples of certain aspects of some embodiments are given. In no way should the following examples be read to limit, or define, the entire scope of the invention.

EXAMPLE 1

A prototype chip was fabricated in 0.35-μm two-poly four-metal (2P/4M) CMOS as shown in FIG. 5, measuring 3.3 mm×3.3 mm including the bonding pads. This example discusses the measurement results from benchtop characterization and acute biological experiments with rats.

Benchtop Characterization

The top plots in FIG. 6 depict the measured frequency response and input-referred noise voltage spectrum of the analog recording front-end for three different bandwidth settings and with the midband ac gain nominally set to 60 dB. The low cutoff frequency could be programmed from 1.1 to 525 Hz, whereas the high cutoff frequency could be adjusted in the range of 5.1 to 12 kHz. The midband ac gain was measured to be 51.9, 57.4, 59.9 and 65.6 dB when the $G_m$-C HPF was bypassed. The gain dropped by ~0.3 dB when the HPF was included in the signal path. With the bandwidth set to 1.1 Hz to 12 kHz, the thermal noise level was measured to be 21 nV/rtHz at 1 kHz. This level increased as the bandwidth decreased, because the LNA input transistors carried less current, increasing their thermal noise contribution. With the same bandwidth setting, the total input noise voltage was measured to be 3.12 $\mu V_{rms}$ by integrating the noise spectrum from 0.5 Hz to 50 kHz, indicating an increase of only 8.2% due to flicker noise. This led to a noise efficiency factor (NEF) of 2.68 for the LNA. The flicker noise corner frequency was measured to be <90 Hz for all bandwidth settings, indicating that the $G_m$-C HPF could largely reduce the flicker noise contribution.

A sinusoidal signal with varying amplitude and frequency was then applied to the LNA input and the signal-to-noise and distortion ratio (SNDR) was measured at the ADC output. FIG. 6(c) shows the measured SNDR at 1 kHz versus input amplitude for the four available gain settings. Lower gain values provided higher input dynamic range, whereas higher gain values provided better signal resolution. FIG. 6(d) depicts the measured SNDR versus input frequency. In the frequency range of 100 Hz to 10 kHz for extracellular neural spikes, the recording front-end provided >41.8 dB of accuracy.

The top plots in FIG. 7 depict the measured microstimulator output current versus its output voltage in the anodic and cathodic phases for four different DAC input codes. The stimulator output voltage could reach at least 4.68 V (going toward 5 V) and 150 mV (going toward 0 V) with a 5-V supply. To further examine the microstimulator functionality, it was interfaced with a silicon-substrate micromachined electrode with stimulus sites of iridium oxide (IrO). FIGS. 7(c) and (d) depict the measured monophasic and asymmetric biphasic stimulus current waveforms delivered by the chip to saline via the microelectrode. The power consumption per channel was measured to be 3.5 μW from 5 V, when the microstimulator generated the biphasic waveform in FIG. 7(d) at a rate of 33 Hz. Table 1 summarizes the measured performance of major circuitry.

TABLE 1

Summary of Measured Performance

| Recording Front-End | |
|---|---|
| AC Gain @ 1 kHz | 51.9, 57.4, 59.9, 65.6 dB |
| Low Cutoff Freq. | 1.1~525 Hz |
| High Cutoff Freq. | 5.1~12 kHz |
| Total RMS Input Noise Voltage | 3.12 μV (BW of 12 kHz) |
| | 3.42 μV (BW of 5.1 kHz) |
| NEF | 2.68 (BW of 12 kHz) |
| | 2.9 (BW of 5.1 kHz) |
| CMRR @ kHz | >56 dB |
| PSRR @ 1 kHz | >65 dB |
| Crosstalk | <−72 dB |

TABLE 1-continued

Summary of Measured Performance

| | |
|---|---|
| Max. Sampling Freq. | 63 kS/s |
| INL/DNL | <±0.8 LSB |
| ENOB | 9.2b ($f_{in}$ = 1 kHz, $f_s$ = 35.7 kS/s) |
| | 9.1b ($f_{in}$ = 1 kHz, $f_s$ = 63 kS/s) |
| Power Consumption* | |
| Amp-HPF | 26.9 µW (BW of 12 kHz) |
| SAR ADC | 19.9 µW (BW of 5.1 kHz) |
| | 5.9 µW ($f_{CLK}$ = 1 MHz) |
| Digital Signal Processing Unit | |
| HPF Cutoff Freq. | 366/756 Hz ($f_{CLK}$ = 1 MHz) |
| Power Consumption | 12.4 µW ($f_{CLK}$ = 1 MHz) |
| Relaxation Oscillator | |
| Output Frequency | 420 kHz~2.5 MHz |
| Supply Sensitivity | −60 kHz/V |
| Power Consumption | 20.8 µW ($f_{CLK}$ = 1 MHz) |

Microstimulating Back-End

| | Anodic | Cathodic |
|---|---|---|
| Stimulus Waveform | Asymmetric Biphasic & Monophasic w/Passive Discharge | |
| Output Current | 0~94.5 µA | 0~31.5 µA |
| Current Pulsewidth | | |
| Monophasic | 0~1.008 ms | N/A |
| Biphasic | 0~240 µs | 0~720 µs |
| Output Impedance | ~400 MΩ | ~440 MΩ |
| DAC Resolution | 6b | |
| DAC Linearity | <±1.6 LSB | |
| Supply Sensitivity | −70.4 nA/V | −10.4 nA/V |
| Voltage Compliance | | |
| Monophasic | 4.68 (of 5 V) | N/A |
| Biphasic** | 3.18 (of 3.5 V) | 1.35 (of 1.5 V) |
| Current Efficiency | 95.6% ($I_{out}$ = 94.5 µA) | N/A |

1.5-to-5 V Converter

| | |
|---|---|
| DC Output Voltage | 4.86~5.35 V |
| Output Ripple | 40 mV$_{pp}$ |
| Max. Load Current | 88 µA ($V_{out}$ = 5.05 V) |
| Power Efficiency | 31% ($V_{out}$ = 5.05 V) |
| RF Transmitter | |
| Comm. Scheme | FSK @ 433 MHz |
| Received Power @ 1 m | −55 dBm (18-cm monopole TX and RX Antennae) |
| Power Consumption | 200 µW |

Total Power for Two Modules w/o RF TX (Stimulation Rate = 33 Hz, Recording BW = 525 Hz~5.1 kHz) = 375 µW
*Per channel In Vivo Characterization In the first biological experiment, a silicon microelectrode with recording sites of iridium was implanted in the somatosensory cortex of a rat's brain and externally interfaced with a single channel of the recording front-end on the chip. The left plot in FIG. 8 shows a 4-s snapshot of the extracellular neural spikes recorded wirelessly at the output of the ADC. In another test, a tungsten electrode with impedance value in the range of 50 to 100 kΩ was placed in the cortical motor area and externally interfaced with a single channel of the microstimulating back-end on the chip to stimulate the brain with a train of 13 monophasic current pulses (90 µA, 192 µs, 300 Hz). The right plot in FIG. 8 depicts the evoked electromyogram (EMG) signal recorded from the rat's neck muscle. The largest EMG spike appeared in <50 ms from the stimulation onset. The chip was then interfaced with the two implanted electrodes to demonstrate activity-dependent ICMS and programmed with the time-amplitude window discriminator parameters determined empirically prior to the experiment. In the first test, the recording and stimulation electrodes were each connected to a single channel of the front- and back-end on the chip, respectively. As the chip operated fully autonomously from a 1.5-V battery, it successfully delivered electrical stimuli to the cortical motor area triggered by neural spikes discriminated on the adjacent electrode in the somatosensory cortex, producing an artificial connection between the two brain regions. FIG. 9 shows the superimposed spike waveforms and corresponding stimulus artifacts from single-pulse stimulation (90 µA, 192 µs) with spike-stimulus delays of 5 and 20 ms. The stimulus artifact rejection mechanism in the recording front-end was de-activated in this test. Hence, artifacts of <4 ms in duration were observed on the recording electrode.

Finally, while the stimulation electrode remained connected to a single channel of the back-end, the multisite recording electrode was connected to all four channels of the front-end in one module. The decision-making circuitry was programmed to trigger ICMS whenever neural activity would be present on any two or more data channels. FIG. 10 shows a 300-ms snapshot of the recorded data of each channel at the output of the digital HPF along with the corresponding spike discriminator output (SDO) and the resulting stimulus trigger signal. Two large stimulus artifacts were distinguishable on each channel. The first stimulation was triggered by neural activity on channels 2 and 3, whereas the second was due to neural activity on channels 2 and 4. Some recorded spikes (marked by black arrows) were not discriminated by the DSP unit due to blanking of its operation after discriminating the spikes that immediately preceded them. This can be alleviated by reducing the time duration of DSP blanking.

As seen in FIGS. 9 and 10, stimulus artifacts are used in this work to show that stimulation is occurring in vivo. However, to address the concern of artifacts false-triggering the microstimulator, a time-amplitude window discriminator is used (as opposed to simple spike thresholding) to discriminate between neural spikes and stimulus artifacts by proper adjustment of time-amplitude window parameters. Blanking the DSP operation after spike discrimination also prevents false-triggering the stimulator by the incoming stimulus artifact. Another concern related to stimulus artifacts is that any spike activity that occurs within the duration of the artifact cannot be detected by the system for triggering purposes. This is less of a concern for activity-dependent microstimulation, since we do not foresee a need to use every single spike in the system to entrain a neuronal population to another group of neurons. Nonetheless, we are developing an integrated signal-processing solution for real-time stimulus artifact rejection, which affords to retain signal information during each stimulation cycle. Such capability may be added to the DSP unit.

LNA Noise Analysis

This section presents a noise analysis for the selected LNA topology and obtains a minimum NEF for a practical design given our technology parameters and supply voltage. FIG. 11 shows a simplified schematic of the LNA and its core operational transconductance amplifier (OTA) for this analysis. We also model the transistor thermal noise current as $$\overline{i_n^2} = 4KT \times \gamma \times g_m \quad (1)$$

where K is the Boltzmann's constant, T is the absolute temperature, $g_m$ is the transistor transconductance, and γ is ⅔ for a transistor operating in strong inversion (above-threshold) and 1/(2κ) for a transistor operating in weak inversion (subthreshold) in which κ is the subthreshold gate coupling coefficient with a typical value of 0.7. The transistor transconductance can be estimated as $$g_m \approx \frac{\kappa \times I_D}{V_{th}} \quad \text{Weak inversion (subthreshold)} \quad (2)$$

$$g_m \approx \frac{2 \times I_D}{V_{OD}} \quad \text{Strong inversion (above-threshold)}$$

where $V_{th}$ is the thermal voltage, $I_D$ is the transistor drain current, and $V_{OD}$ is the transistor overdrive voltage. Assuming that the overall transconductance of the OTA, $G_m$, is nearly equal to that of transistor $M_1$, the input-referred noise voltage of the OTA can be estimated as $$\overline{V_{n,OTA}^2} = \frac{1}{g_{m1}^2}\left(\frac{4KT}{\kappa} \times g_{m1} + \frac{16KT}{3} \times g_{m3} + \frac{16KT}{3} \times g_{m7}\right). \quad (3)$$

To minimize the OTA input noise voltage, $M_{1,2}$ operate in subthreshold to maximize $g_{m1}$ for a given current level, whereas $M_{3,4,7,8}$ operate in strong inversion to reduce their transconductances. Moreover, the drain current of $M_{1,2}$ is selected to be much larger than that of $M_{7,8}$ in the folded branch. This current scaling scheme helps improve the OTA noise performance by further increasing $g_{m1}$ and reducing $g_{m7,8}$. Therefore, neglecting the noise contribution by $M_{7,8}$, (3) can be simplified as $$\overline{V_{n,OTA}^2} = \frac{1}{g_{m1}} \times \frac{4KT}{\kappa}\left(1 + \frac{8}{3} \times \frac{V_{th}}{V_{OD3}} \times (\beta + 1)\right) \quad (4)$$

where $\beta = I_7/I_1$ is the current scaling factor between the input differential pair and the folded branch. Equation (4) suggests that $V_{OD3}$ should be increased to reduce the OTA input noise. However, increasing $V_{OD3}$ means the drain-source voltage of $M_{3,4}$ should be increased too, limiting the OTA output voltage swing. For a peak-to-peak voltage swing ($V_{Swing}$) of 0.5 V at the OTA output, an upper limit of 0.5 V can be found for $V_{OD3}$ given a supply voltage of 1.5 V. It should be noted that $V_{Swing}$ of 0.5 V allows the LNA to handle input signals as large as ~±6 mV, in case local field potentials (LFPs) or other low-frequency artifacts would also be present at the input. In this work, $M_{3,4}$ are sized for $V_{OD3}$ of 0.35 V instead to ensure that they do not enter the triode region in the presence of process parameter variation.

According to (4), the OTA input noise voltage also depends on β, indicating that the current scaling factor should be selected judiciously. To that end, we next investigate the effect of β on the overall OTA transconductance, $G_m$. In a similar way, the analysis of the proposed circuit reveals the $G_m$ to be $$G_m \approx \frac{g_{m5}}{g_{ds1} + g_{ds3} + g_{m5}} \times g_{m1} \quad (5)$$

where $g_{ds}$ is the transistor drain-source conductance. Since the channel length of $M_{3,4}$ is selected to be much longer than that of $M_{1,2}$, $g_{ds3}$ is much smaller than $g_{ds1}$, which yields $$\frac{G_m}{g_{m1}} \approx \frac{1}{1 + \frac{V_{th}}{\kappa \times V_{A1} \times \beta}} \quad (6)$$

where $V_{A1}$ is the early voltage for $M_1$ (i.e., $1/\lambda_1$) and $M_5$ is sized to operate in subthreshold. This equation is also plotted in FIG. 11 with a value of 20 V for $V_{A1}$. According to (4), reducing β helps reduce the OTA input noise voltage, but β cannot be reduced arbitrarily to ensure that $G_m$ is not degraded considerably (i.e., β≥0.05 from FIG. 11).

Another important consideration in selecting β is the sensitivity of bias currents to transistor mismatches in the OTA and associated biasing circuitry. Assume that $\Delta I_1$, $\Delta I_3$ and $\Delta I_1$ are bias current deviations from their corresponding nominal values due to transistor mismatches. If $\Delta I_1$ and $\Delta I_3$ are assumed to be uncorrelated, it can be shown that $$\frac{\Delta I_7}{I_7} = \sqrt{\frac{\Delta I_1^2 + \Delta I_3^2}{I_7^2}} \quad (7)$$

$$= \frac{1}{\beta} \times \sqrt{\left(\frac{\Delta I_1}{I_1}\right)^2 + (\beta + 1)^2 \times \left(\frac{\Delta I_3}{I_3}\right)^2}.$$

For example, for a β value of 0.05, a 2% variation in $I_1$ and $I_3$ causes a 58% variation in $I_7$, which might adversely affect the OTA operation and degrade its transconductance. In this example, the minimum value of β (when LNA bandwidth is maximum) is selected to be 0.091 for which $G_m$ is 98% of $g_{m1}$, and 2% variation in $I_1$ and $I_3$ causes only 32.5% variation in $I_7$. Table 2 tabulates the dimension, current level, and operating condition of each transistor pair in the OTA for optimum noise performance with the maximum bandwidth setting.

TABLE 2

Dimension, Current Level, and Operating Condition of OTA Transistors

| Transistor | Dimension (µm) | Current Level (µA) | Simulated $g_m$ (µS) | Inversion Coefficient* | Operating Condition |
|---|---|---|---|---|---|
| $M_{1,2}$ | 800/2 | 2.75 | 76 | 0.021 | subthreshold |
| $M_{3,4}$ | 20/20 | 3.00 | 16 | 26.8 | above-threshold |
| $M_{5,6}$ | 80/1.3 | 0.25 | 6.9 | 0.036 | subthreshold |
| $M_{7,8}$ | 4/40 | 0.25 | 2.5 | 7.6 | above-threshold |

*$\mu_n C_{ox} = 170\ \mu A/V^2$, $\mu_p C_{ox} = 58\ \mu A/V^2$

To compute the NEF, we should note that the input-referred noise voltage of the LNA is almost equal to that of the OTA given that the parasitic gate capacitance at the input terminals of the OTA is typically much smaller than $C_{1,2}$. The NEF can be calculated $$NEF = V_{ni,rms} \times \sqrt{\frac{2 \times I_{total}}{\pi \times V_{th} \times 4KT \times BW}} \quad (8)$$

where $V_{ni,rms}$ is the rms input noise voltage of the LNA, $I_{total}$ is the total supply current, and BW is the 3-dB bandwidth of the amplifier. Finally, assuming that the LNA has a single dominant pole in its frequency response and noting that $I_{total} = 2 \times I_3$, combining (4) and (8) yields $$NEF = \sqrt{\frac{2\times(\beta+1)}{\kappa^2} \times \left(1 + \frac{8}{3} \times \frac{V_{th}}{V_{OD3}} \times (\beta+1)\right)} \quad (9)$$

which results in an NEF of 2.33 for β of 0.091 and $V_{OD3}$ of 0.35 V. Hence, the NEF of 2.68 derived from measured performance of the LNA (when set for maximum bandwidth) is in good agreement with this analysis. This argument also shows that reducing the supply voltage can adversely impact the OTA noise performance for the same output voltage swing, making it challenging to reduce the power supply (or $V_{DD}$) below 1.5 V in this architecture.

Other embodiments of a neural prosthetic device might require 16, 32 or even higher number of recording and stimulating channels, resulting in higher power consumption and larger silicon area. FIG. 12 shows a breakdown of the area and power consumption for the entire SoC, including both modules. The core area of the SoC excluding I/O pads is 2.6×2.6 mm², of which 34% is occupied by the 1.5-to-5-V converter. In this work, the converter can provide a maximum dc load current of ~88 μA for an output voltage of 5.05 V, which allows an average stimulus rate of >500 Hz for simultaneous stimulation on all eight channels with maximum stimulus current, given that the microstimulator dissipates 3.5 μW per channel for such stimulation at a rate of 33 Hz. However, with cortical neuronal firing rates of <150 spikes per second, the silicon area of the proposed converter can be reduced by ~63%.

The power pie-chart is generated assuming biphasic stimulation at a rate of 33 Hz (anodic: 94.5 μA, 192 μs; cathodic: 31.5 μA, 576 μs) and recording bandwidth of 525 Hz to 5.1 kHz. Excluding the FSK transmitter, the total power consumption is measured to be 375 μW for two modules with the analog recording front-end being the most power-hungry circuit block. Based on simulation results, if we reduce the LNA bias currents to half their current values (all transistors and capacitors should also be sized down accordingly to maintain the same bandwidth), we can save up to 29% and 20% in silicon area and power consumption of the analog recording front-end, respectively. Although this would increase the LNA total input noise by ~41% to 4.8 $\mu V_{rms}$, it is still less than the background noise of the recording site (5 to 10 μV). Another effective approach to reduce the front-end power consumption and silicon area is to reduce the successive approximation register analog-to-digital converter (SAR ADC) resolution to 9 bits. In the proposed design, the input-referred quantization noise of the SAR ADC ($V_{DD}/(\sqrt{12} \times Gain \times 2^{ENOB})$) is ~0.8 $\mu V_{rms}$ for a nominal gain of 60 dB, which is much less than that of the LNA (~3 $\mu V_{rms}$). Therefore, reducing the SAR ADC resolution by one bit would not degrade the performance considerably. Further, the power consumption of the secondary amplifier (~17% of the total system power) driving the capacitive network of the ADC can be significantly reduced as well by decreasing the ADC resolution.

EXAMPLE 2

This example presents experimental results from biological tests with anesthetized and ambulatory rats using a neural prosthetic device of the present disclosure. The experiments were conducted in the cerebral cortex of adult Long-Evans rats in accordance with guidelines approved by the Institutional Animal Care and Use Committee, Kansas University Medical Center, Kansas City, Kans.

FIG. 13 is an illustration of the experimental setup for this example, using spike-triggered ICMS in an ambulatory rat. An ASIC as depicted in FIGS. 14 and 15, together with a minimum number of external components and a single coin battery (1.55 V), were assembled on a rigid-flex substrate to create a miniature, head-mounted microdevice. Neural data were transmitted wirelessly via a radio-frequency frequency-shift-keyed (RF-FSK) link at ~433 MHz between the microdevice and a commercial RF receiver (AOR, Torrance, Calif.), which down-converts the RF signal to an intermediate frequency (IF) of 10.7 MHz. A wired connection was temporarily attached to the microdevice for programming and monitoring its operation status. A custom external receiver board was used for signal conditioning and decoding of wired and wireless signals. A digital data acquisition (DAQ) card (National Instruments, Austin, Tex.) established a high-speed connection between the receiver board and a PC used for microdevice programming as well as storage and analysis of the recorded data with MATLAB™.

ASIC Overview

FIG. 14 depicts a block diagram and a die micrograph of a 0.35-μm two-poly four-metal (2P/4M) complementary metal-oxide-semiconductor (CMOS) integrated circuit used in this example. Each four-channel module of the integrated circuit incorporates a recording front-end, a digital signal processing (DSP) unit, and a stimulating back-end. For autonomous operation from a single 1.55-V battery, the ASIC also integrated a dc-dc converter that generated 5 V from the battery as the power supply for the stimulating back-end. It was capable of delivering ICMS sequences via an external trigger as well as triggered by neural spikes discriminated in real time, with precise control over the stimulation time instance. The recording front-end featured a bandpass frequency response with the low and high cutoff frequencies programmable from 1.1 to 525 Hz and 5.1 to 12 kHz, respectively, and provided 2b-programmable ac amplification (nominal gain of ~60 dB at 1 kHz), dc input stabilization, and 10b digitization of the recorded neural signals.

The DSP unit used in each module provided additional digital highpass filtering to remove any residual dc offsets or low-frequency artifacts and subsequently performed real-time spike discrimination based on threshold crossing and two user-adjustable time-amplitude windows. The digital highpass filter (HPF) used in the DSP unit had a programmable cutoff frequency of 366 or 756 Hz, given a 1-MHz system clock. If a spike event was accepted on any channel, the corresponding spike discriminator output (SDO) was activated after a programmable time delay (0 to ~28.6 ms).

The decision circuitry then generated any logic combination of SDO 1~4 as a trigger signal for stimulation activation. Upon triggering, the programmable stimulating back-end delivered a charge-balanced asymmetric biphasic stimulus or monophasic stimulus with passive discharge to the neural tissue. The anodic and cathodic current pulse amplitudes were 6b-programmable from 0 to 94.5 μA and 31.5 μA, respectively. With a 1-MHz system clock, the duration of the anodic phase could be programmed from 0 to 240 μs with a resolution of 16 μs, whereas that of the cathodic phase was programmable from 0 to 720 μs with a resolution of 1 μs. For monophasic stimulation, the duration of the constant-current phase was programmable from 0 to 1.008 ms with a resolution of 16 μs. Passive discharge was performed after each constant-current phase to drain the accumulated charge on the stimulation site via a 2b-programmable resistor.

In constructing the head-mounted microdevice, one four-channel module of the ASIC was used for spike-triggered ICMS. Further, in the nominal operating condition of the ASIC, the bandwidth of the recording front-end was set to be 525 Hz to 5.1 kHz and the cutoff frequency of the digital HPF was set to 366 Hz. The stimulating back-end was also programmed to deliver a single monophasic current pulse (duration of 192 µs) with variable amplitude followed by passive discharge, upon receiving an external or neural-based stimulus trigger.

FIG. 15 shows the block diagram and a photograph of the assembled microdevice used in this example with an ambulatory rat. Various components were assembled on a four-layer rigid-flex printed-circuit board (PCB) made from FR-4 and polyimide (Flexible Circuit Technologies, Plymouth, Minn.). The microdevice was connected to two chronically implanted recording and stimulation microelectrodes via two microconnectors (Omnetics Corporation, Minneapolis, Minn.) in plug-and-play fashion. The microelectrodes were not permanently connected to the microdevice in order to allow replacement of the microdevice in case of failure or for reuse in additional experiments. The flexible polyimide interconnect between the microelectrode connectors and the rigid substrate allowed for some adjustability in microelectrode placement during implantation, simplifying the surgical procedure. For safe operation, four dc-blocking capacitors (220 nF) were placed in series with the stimulation channels to prevent any net dc current flow into the tissue, potentially arising from semiconductor failure or charge imbalance. A 6.8-mm, 1.55-V, silver-oxide, coin battery with capacity of 26 mAh (Energizer, St. Louis, Mo.) was selected to power the microdevice due to its small size and stable output voltage. The onboard battery powered the device continuously at its nominal operating condition for 24 hours.

A low-power, low-voltage, commercial microcontroller (ST Microelectronics, Geneva, Switzerland) programmed the ASIC during power-up and then shut down to reduce the static power consumption. The ASIC checked the validity of the programming parameters using two 10b redundant codes. If both codes in the parameter data stream were equal to those hardwired inside the chip, the Check signal was activated; otherwise, the ASIC sent an interrupt signal to the microcontroller to turn it back on for reprogramming. A new parameter data stream could be sent to the microcontroller from the PC via the external receiver board using a bidirectional RS232 asynchronous serial link. The data were saved inside the microcontroller EEPROM and then shifted into the chip. Once ASIC programming was successful, the microcontroller transmitted an acknowledgment signal back to the PC.

The FSK wireless link in the microdevice could transmit either the full-voltage record on one channel or spike discrimination events on all four channels to the RF receiver placed as far as 2 m from the rat. A 5-cm twisted wire was used as the antenna connected to one side of an external resonant inductor (33 nH)-capacitor (3.9 pF) LC tank. These LC components resulted in an RF link frequency of ~433 MHz, given a tolerance of 5% in their values and parasitic contribution by input-output (I/O) pads, wire bonds, and PCB interconnects. The wireless recording of broad-band neural data was limited in this example to a single channel due to battery lifetime considerations for supporting higher data rates. Nonetheless, the raw data recorded on all four channels of the microdevice could still be accessed simultaneously using a wired link between the microdevice and the external receiver board. The wired connection also can provide the output voltage level on all four stimulation channels to monitor stimulation site impedance during long-term experiments.

A commercial low-dropout (LDO) voltage regulator (ST Microelectronics, Geneva, Switzerland) together with four external capacitors were used to isolate the power supply line of the sensitive front-end recording circuitry from that of the rest of the system, mainly the noisy digital circuitry and 1.5-to-5V converter. Given the non-zero source impedance of the silver-oxide coin battery (5 to 10Ω), this scheme was critical to ensure robust, reliable operation of the sensitive recording front-end. Although the power supply rejection ratio (PSRR) of the recording front-end was measured to be >65 dB, this measurement is typically done with the input shorted to ground. As depicted schematically in FIG. 16, the combination of the recording microelectrode capacitance $C_E$ and parasitic capacitors $C_{P1,2}$ in the analog I/O block contributed by electrostatic discharge protection circuitry and bonding pad created an additional signal path for the supply-induced noise that can degrade the PSRR in practice. From FIG. 16, the PSRR through I/O parasitic capacitors could be derived as $$PSRR_{I/O} = \frac{C_E + C_{p1} + C_{p2} + C_{IN}}{C_{P1}} \cong \frac{C_{IN} + C_E}{C_{P1}}$$

where $C_{IN}$ is the input capacitance of the recording front-end, which is 28 pF in this example. Given $C_E$ of 150 pF (i.e., recording site impedance of ~1.1 MΩ at 1 kHz) and estimated values of 1 pF for $C_{P1,2}$, the above equation results in $PSRR_{I/O}$ of 45 dB. FIG. 16 also shows the measured PSRR with $V_{IN}$ shorted to ground as well as that with $V_{IN}$ connected to ground via a 150-pF external capacitor. $PSRR_{I/O}$ was measured to be ~44 dB at 1 kHz, in good agreement with the above equation. Therefore, measured noise of 10 mV$_{pp}$ on the battery voltage would induce ~63-µV$_{pp}$ noise on the input, greatly degrading the recording signal-to-noise ratio. Instead, the LDO regulator attenuated the power supply noise by more than 60 dB at 1 kHz, reducing the noise induced on the input well below the thermal and flicker noise levels of the recording front-end.

External Receiver Board

FIG. 17 shows the block diagram and a photograph of the custom external receiver board used in this example. It incorporated FSK demodulation circuitry using a commercial phase-locked loop device (NXP Semiconductors, The Netherlands), which detected the frequency variation of the amplified/filtered 10.7-MHz IF signal for further down-conversion to baseband. The wirelessly received data together with four channels of wired data were processed in a complex programmable logic device (Altera, San Jose, Calif.), which used a Manchester decoder for clock/data recovery and sent the signals to the PC via the DAQ card. Any one of the five data channels could be selected by the user for broadcasting of the data stream through a speaker. Specifically, a preamble detector and a deserializer unit convert the selected data stream to 10b digital codes that are then converted to an analog audio signal using a digital-to-analog converter (Analog Devices, Norwood, Mass.). This feature allowed a trained user to rapidly identify whether neural activity was present in the recorded data stream by listening to the sound of spiking neurons. The onboard microcontroller unit received parameter data for microdevice operation from the PC and sent them to the microdevice via a RS232 asynchronous serial link. As stated previously, if ASIC programming is successful, the microcontroller receives an acknowledgment signal from the microdevice and then sends the programming status back to the PC.

Experiments With Anesthetized Rats

Microelectrodes were acutely implanted in two spatially separated forelimb motor areas of the rat's brain that are reciprocally connected with one another. Specifically, a micromachined silicon microelectrode with recording sites of iridium (NeuroNexus Technologies, Ann Arbor, Mich.) with impedance values of 2 to 3 MΩ was implanted in the rostral forelimb area (RFA) within the premotor cortex, and a tungsten, matrix, stimulation electrode (FHC, Bowdoin, Me.) with impedance value of 50 to 100 kΩ was implanted in the caudal forelimb area (CFA) within the primary motor cortex. Each electrode was externally interfaced with a single data channel of the recording front-end and stimulating back-end on the ASIC. A connection to the animal tail was tied to the system ground and used as a reference electrode for both recording and stimulation. In the first experiment, the CFA was stimulated at 2 Hz with a single monophasic current pulse [90 μA, 192 μs, see FIG. 18(a)], using an external trigger signal. FIG. 18(b) shows three traces of the recorded data from the RFA, depicting stimulus artifacts with duration of ~4 ms and four neural spikes detected by the ASIC shortly after stimulation. FIG. 18(c) shows the raster plot and peristimulus histogram of the neural response to ICMS for a total of 315 ICMS pulse, depicting a clear increase in neural activity 7.5 ms after stimulation. This example demonstrates, inter alia, the system capability for simultaneous stimulation and recording the neural response to ICMS.

In a second acute experiment, neural activity was recorded on all four channels of the ASIC front-end to perform multi-channel spike-triggered ICMS. If a spike event was accepted on any channel, the corresponding SDO was activated for 10 ms after a time delay of 5 ms. The decision circuitry was programmed to trigger ICMS whenever neural activity was simultaneously present on channels 2 and 3. FIG. 19 shows the simultaneously recorded data on each channel at the output of the digital HPF along with the corresponding SDO and the resulting stimulus trigger signal during a 300-ms time window. Two large stimulus artifacts were distinguishable on each channel as a result of spike-triggered stimulation, when simultaneous spike events (within a 10-ms window) occurred on channels 2 and 3. The data in both acute experiments were recorded via the wired link.

Experiments With Ambulatory Rats

Two micromachined silicon microelectrodes (NeuroNexus Technologies, Ann Arbor, Mich.) were chronically implanted in the RFA and second somatosensory area (SII) of the rat's brain for recording and stimulation, respectively, using standard neurosurgical techniques. The recording microelectrode had sixteen 413-μm² iridium sites uniformly placed along the length of its 3-mm silicon shank. The stimulation electrode had sixteen 1250-μm² sites uniformly placed along its 2-mm shank. The stimulation sites were also activated with iridium oxide (IrO) to further reduce the site impedance to ~60-120 kΩ. A stainless steel threaded rod was mounted through an opening in the skull and affixed to it with acrylic. As shown in FIG. 20, the microdevice was mounted ~1 cm above the rat's head and affixed to the skull using the threaded rod and nut, in such a way that the rat could not reach the microdevice. The threaded rod was also tied to the system ground and used as a reference electrode for both recording and stimulation.

Spontaneous neural activity was recorded on two of the four recording channels (Channels 3 and 4). The top two plots in FIG. 21 depict the data recorded at the output of the digital HPF within a 3-s window, and the bottom two plots depict the superimposed, time-aligned spike waveforms that crossed the user-positioned 20-μV threshold level (red dashed line). The accepted spikes (indicated with blue markers in top and as dark gray in bottom plots) also passed through the two time-amplitude window discriminators (solid red boxes), whereas the waveforms in light gray were rejected by the spike discriminator (i.e., not used for stimulus triggering).

The microdevice was programmed to trigger ICMS on all four stimulation channels using accepted spikes recorded on channel 4. Upon each trigger, the microdevice delivered a single monophasic current pulse (30 μA, 192 μs) with passive discharge to stimulate the target cortical tissue. The DSP operation was also blanked for ~28.5 ms after each spike discrimination (i.e., neural spikes on channel 4 did not trigger ICMS during this period). FIG. 22 shows the superimposed spike waveforms and corresponding stimulus artifacts from single-pulse stimulation with spike-stimulus delays of 5 and 7.5 ms. The data were recorded wirelessly as the microdevice operated autonomously from a single 1.55-V battery.

The recorded data from channels 3 and 4 (corresponding to the spike-stimulus delay case of 7.5 ms) were further analyzed to investigate whether spike-triggered ICMS induced any electrophysiological change in the cortical circuitry. This was intended to show the physiological effect of the stimulating electrode beyond simply showing the stimulus artifact. The top left plot in FIG. 23 depicts a 34-ms window of the recorded data on channel 4, showing the trigger spike, the resulting stimulus artifact, and three other spikes that occurred during the DSP blanking period (indicated by red markers). The middle left plot depicts the peristimulus histogram (1-ms bins) during the DSP blanking period for 3600 trials. The trigger spikes occurred just prior to the start of the histogram. The histogram suggests that the neuronal firing rate after ICMS was lower than that prior to stimulation. A paired T-test also confirmed that the reduction of the neuronal firing rate after ICMS was statistically significant with $p<0.0001$. The bottom left plot depicts the mean neuronal firing rate (±99% confidence interval) before and after ICMS on channel 4. The same effect was also observed on channel 3 as shown in the plots on the right, although generally fewer spikes were recorded on that channel throughout the experiment.

To determine whether the firing rate returned to baseline levels after the cessation of stimulation, the effect of spike-triggered ICMS over a much longer time scale was examined, beginning ~90 s before stimulation, then during the 500-s stimulation period, and for ~410 s after stimulation (see FIG. 24.) The top plot depicts the measured stimulation rate versus time, whereas the middle and bottom plots depict the mean neuronal firing rate on channels 3 and 4, respectively. The data were smoothed by applying a moving average with a 25-s time window. The dashed lines show the average level for each section of the plot in time. FIG. 24 clearly shows that the neuronal firing rate not only decreases during spike-triggered ICMS, but also that it returns to the pre-stimulus level once ICMS is terminated.

Further, as expected, the stimulation rate is slightly below the neuronal firing rate on channel 4 during ICMS, because the spike events on channel 4 that occur during the DSP blanking period do not trigger stimulation. The reduction in spiking rate of channel 4 (and to a lesser extent, channel 3) is likely the result of activating horizontal connections that project from the point of stimulation to the recording site. These projections can innervate inhibitory interneurons that, when activated, would lead to a reduction of the activity of the recorded neurons.

EXAMPLE 3

Methods

Animals

Fifteen Male Long-Evans rats (350-450 g) were obtained from Harlan. At approximately four months of age, animals were randomly assigned to one of three groups: activity-dependent stimulation (ADS; n =6), randomized open-loop stimulation (OLS; n =5), or no stimulation (Control; n =5). Rats were housed individually and were maintained on a 12:12 h light:dark cycle. Rat chow was provided (3-5% body weight) on a feeding schedule to promote compliance on behavioral tasks and was supplemented with rodent food pellets during the skilled reaching task. Protocols for animal use were approved by the University of Kansas Medical Center Institutional Animal Care and Use Committee (IACUC) and adhered to the Guide for the Care and Use of Laboratory Animals (National Research Council, 1996).

Behavioral Training

Skilled Reach Test. Each animal was put into a Plexiglas reaching chamber and a single banana-flavored food pellet (45 mg, Bioserv) was placed into a shallow food well 2 cm from the front wall on an external shelf positioned 3 cm from the bottom of a 10-in$^3$ chamber (Withers and Greenough, 1989; Bury and Jones, 2002; Hsu and Jones, 2005). The opening of the chamber was such that only the left forelimb could be used for reaching. Prior to entry into the remainder of the study, the animal was required to reach and retrieve food pellets above 70% success for three consecutive days. The percentage of successful retrievals was based on the number of successful pellets grasped, retrieved, and brought to the animal's mouth during a total of 60 trials. Probe trials occurred on Days 3, 5, 8, 14 and 21 following an infarct within the forelimb motor area of the cerebral cortex and consisted of 20 trials with microdevice stimulation on and 20 trials with microdevice stimulation off.

Surgical Procedures

Animals were initially anesthetized with ketamine (100 mg/kg i.p.) and xylazine (5 mg/kg i.m.), prior to being placed within a stereotaxic frame, and given supplements of ketamine (20 mg/kg i.m.) during the surgical procedure as needed. A midline incision was made to expose the skull surface, then a 5-mm trephine hole was made over the right hemisphere using stereotaxic coordinates to expose the CFA centered at +0.5 mm rostral, +2.5 mm lateral relative to bregma. Two 1-mm burr holes were made over a secondary motor area, the RFA, and the hand area of primary somatosensory cortex (S1) in the right hemisphere using corresponding stereotaxic coordinates (+3.5, +2.5 and −1.25, +4.25, respectively). Three additional burr holes (0.625 mm) were made for skull screws, one along the lateral ridge on either parietal bone, and one in the center of the interparietal bone. The dura was resected over S1 and RFA, but left intact over CFA.

Defining Physiological Areas

The RFA and S1 areas were isolated using electrophysiological mapping techniques. Burr holes over each area allowed up to 12 sites to be tested at 250-μm resolution. To verify the RFA, a 16-channel Michigan electrode (NeuroNexus Technologies) was inserted into the burr hole to a depth of 1700 μm and intracortical microstimulation was delivered as a 40-ms train of thirteen, 0.2-ms monophasic cathodal pulses delivered at 333 Hz at the rate of one train per second (TDT). During stimulation, the current delivered was gradually increased from 1 μA to 80 μA. Upon stimulation, the animal was visually observed for evoked movements. Forelimb movements that were bounded caudally by neck/trunk responses were considered within RFA. To verify S1, a Michigan electrode was inserted into the burr hole and the neural signal was amplified and fed into a speaker and a digital display. The left forelimb was palpated until the touching could be correlated with both the amplified sound of the neural activity and spikes on the display (TDT). The hand area of S1 was defined by evoked responses that could be localized to cutaneous stimulation of the wrist, hand, or digit. Both RFA and S1 were found in each animal before proceeding with the cortical impact.

Cortical Impact

After defining RFA and S1, a controlled cortical impact was delivered to CFA using the Impact One stereotaxic impactor (Leica Microsystems). The impact was delivered via a flat, circular tip with a 3-mm diameter. The impactor tip was fully extended and then slowly lowered onto the surface of the dura. Contact with the dura was indicated by an audio signal triggered by a feedback sensor. The impactor tip was then retracted within the impactor arm, and the arm was then lowered 2 mm. Once triggered, the impactor tip accelerated at 1.5 m/s extending 2 mm below the surface of the dura. The impactor tip remained extended for 100 ms then automatically retracted, leaving the dura intact.

Microdevice Implantation

Following the impact, skull screws were implanted into the parietal bones, and a threaded rod was implanted into the interparietal bone. These were affixed to the skull with dental acrylic. A hybrid, 16-channel, chronic Michigan probe for recording was inserted into the area defined as RFA using a micropositioner. The probe and burr hole opening were then sealed with a silicone polymer (Kiwk-Cast, WPI). The base of the probe connector was lowered onto the dental acrylic and fixed into place. An activated, 16-channel, chronic Michigan probe for stimulation was inserted into the area defined as S1 hand area and fixed into place in the same manner as above. Any remaining exposed areas were covered with the silicone polymer before suturing the incision. The microdevice was then affixed to the threaded rod with stainless steel nuts and spacers, and its connectors plugged into those of the appropriate electrodes. Technical aspects of the microdevice were described elsewhere (Azin et al., 2011a,b), but in short, the microdevice was able to autonomously record from up to four of the 16 channels of the recording microelectrode located in RFA, amplify and digitize the neural signals, and employ a user-programmable spike discrimination algorithm to trigger activity-dependent stimulation pulses delivered to the microelectrode implanted in S1 hand area.

Electrophysiological Recording

Initial Programming. Two to four hours following the microdevice implantation, a 1.55-V battery was inserted into the microdevice. An Omnetics connector leading to a custom-built controller board was plugged into the microdevice, and the microdevice was initially programmed to record on all four available channels. Signals from these four channels were recorded from the microdevice and routed through the controller board to a LabVIEW data acquisition card. The signals were monitored in real time through both software and an amplified audio signal from the controller board. The highpass-filtered signal from one of the four channels was exported to MATLAB™ and loaded into a spike discrimination script within MATLAB™. A threshold level was defined above the noise level of the signal, and small segments of waveforms that crossed the threshold level were overlaid on each other at the threshold crossing point. Spikes were then defined by two user-adjustable time-amplitude windows, with the priority of maximizing detection of observed spikes while avoiding noise and/or stimulus artifacts. Once the spike discrimination parameters were defined, they were imported into the microdevice programming software. Stimulation parameters were also set in the software to a 60-μA current delivered pseudo-biphasically with pulse duration of 192 μs. For the ADS group, stimulation was set to occur 7.5 ms following spike discrimination on the channel from which the parameters were derived. For the OLS group, stimulation current and pulse duration were the same as for the ADS group, and pulses were pseudo-biphasic. However, the stimulator was not dependent upon recorded signals in RFA. Instead, the stimulation occurred independently throughout the post-lesion period with inter-stimulus intervals ranging from 35 to 200 ms. This range of inter-stimulus intervals was derived from prior data using ADS and corresponded with the most common range of stimulation frequencies of the ADS group. Any individual inter-stimulus interval (and hence, frequency of stimulation) chosen was randomized equally across the range to more closely approximate the level of stimulation the ADS group received.

Finally, the output was programmed to transmit the data through either a wired connection or a wireless connection. The microdevice was reprogrammed and additional recordings were taken to assess the spike discrimination parameters. The microdevice was then programmed to transmit the data wirelessly, and the animal was allowed to move freely about its cage.

Signal Maintenance. The microdevice consumed power at a level to necessitate battery changes once daily for ADS and twice daily for OLS groups. Each animal's microdevice was tested a minimum of once a day to confirm its functionality. Occasionally, there was a discrepancy between spikes observed on the monitoring software and spikes actually being detected. When this occurred, the microdevice was reconnected to the wired connection, the stimulation was turned off, and the activity was processed through the spike discrimination software. In order to maximize spike discrimination, the threshold and/or time-amplitude windows were slightly adjusted to compensate for detection failures. If no spiking was detected, the remaining channels were monitored. If there was signal on one or more of the remaining channels, the stimulation trigger was moved to the most active channel. If no activity was detected on all four channels, the microdevice was removed and the microelectrodes were tested with commercial electrophysiology equipment (TDT). If the electrodes were still functional and the animal had not fully recovered from the injury, a new microdevice was attached to the animal and reprogrammed as above.

Behavioral Tasks. During behavioral tasks, the microdevice was reprogrammed so that one half of each behavioral trial was done while the microdevice stimulator was turned on and the other half was done while the stimulator was turned off. Control animals were given equivalent time and trials on the tasks. Except for signal maintenance and dead batteries, this was the only time that the ADS and OLS groups were not receiving stimulation.

Data Recording. The highpass-filtered neural signal was recorded at ~35 kHz from either one or four channels (wireless or wired connection, respectively) during all signal monitoring and behavioral trials using LabVIEW software. In addition, all animals had multiple sessions where data were recorded during home cage behavior. The raw signal recording duration of any single trial was software limited to ~45 min, but the spiking time stamp data could be recorded for up to 24 hours. The neural signal data were converted from a LabVIEW file to a text file and analyzed using custom MATLAB™ software.

Results

The results demonstrated a potent and statistically significant effect of ADS on motor performance after only 8 days of operation. By Day 14 post-lesion, performance in the ADS group was indistinguishable from pre-lesion performance (~70% with stimulation "on" based on linear mixed model, intent-to-treat design; FIG. 25A). The improvement persisted at Day 21 post-injury. In the ADS group, performance in the stimulation on condition increased from 27% on Day 3 post-injury to 39% on Day 5 post-injury, 53% on Day 8 post-injury, and 69% on Day 14 post-injury. The improvement in performance was also evident in the stimulation off condition in the ADS group, and was statistically significant on Days 8, 14 and 21 post-injury.

In contrast, while there was some improvement in the OLS group (statistically significant difference from control animals on Day 21 post-injury; FIGS. 25A and 25B), effects were reduced compared to the ADS group. By Day 14 post-injury, performance was 45% and, based on modeled data, never exceeded 50% in either stimulation on or off conditions. Untreated control animals performed at <25% throughout the recovery period.

Further, there were substantial differences between the on and off states of the microdevice operation during behavioral testing (FIG. 26). In the ADS group, the animals were up to 13% better with the device stimulation on vs. off (FIG. 26). These differences were evident in the ADS group until Day 21 post-injury, when on vs. off states were similar. In individual rats, these differences were quite pronounced on specific days, especially on Days 5 and 8 post-injury. As an example, in one rat on Day 8 post-injury, the difference between the on vs. off states was over 40%, with twice as many pellets retrieved during the on state.

In the OLS group, rats performed slightly worse with the stimulation turned on vs. off (FIG. 26), but this difference never exceeded 7% (Day 3 post-injury). However, some rats performed substantially worse with the stimulation turned on vs. off (Day 3, 14 and 21).

Discussion

The results demonstrate, inter alia, that ADS between the spared premotor cortex (i.e., the RFA) and the somatosensory hand area can result in a rapid improvement in motor function by Day 8 post-lesion, and that the improved function persists through at least Day 21 post-lesion. This is the first demonstration that ADS can be used to positively affect function after cortical injury.

One of the many advantages of the present disclosure is that, in some embodiments, it may provide for a cortical communication bridge allowing distant cortical areas with substantially no effective communication to be artificially linked after injury, which may have widespread clinical application. The results shown in Example 3 demonstrate, inter alia, that somatosensory-motor communication links that are disrupted following TBI can be restored by a microdevice of the present disclosure, thereby promoting restoration of functional movements. It is possible that a microdevice of the present disclosure may also be applied to sensorimotor dysfunction after stroke. It is also possible that a microdevice of the present disclosure may also be applied to certain aphasic conditions after either stroke or TBI. Neuroimaging studies in humans have shown that the arcuate fasciculus connecting Broca's and Wernicke's areas in the brain is altered with specific types of training (Schlaug et al., 2009). It may be possible to use the methods and devices of the present disclosure to automatically aid in the reconnection of this functionally important communication link in the brain to restore language. In addition, there are several neurological and psychiatric disorders that include what has broadly been termed "disconnection syndromes" that could be aided by the methods and devices of the present disclosure. In some embodiments, it is also possible that a microdevice of the present disclosure may provide for a neural communication bridge in cortex or subcortical structures to alleviate functional disorders in idiopathic conditions, i.e., when specific dysfunctional communication cannot be identified. Finally, in some embodiments, it is also possible that a microdevice of the present disclosure may provide for a neural communication bridge in cortex or subcortical structures to improve function or behavioral performance in otherwise healthy brains.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

References

1. M. M. Ahmadi, "A new modeling and optimization of gain-boosted cascode amplifier for high-speed and low-voltage applications," *IEEE Trans. Circuits Syst. II*, vol. 53, no. 3, pp. 169-173, March 2006.
2. A. T. Avestruz, W. Santa, D. Carlson, R. Jensen, S. Stanslaski, A. Helfenstine, and T. Denison, "A 5 µW/channel spectral analysis IC for chronic bidirectional brain-machine interfaces," *IEEE J. Solid-State Circuits*, vol. 43, no. 12, pp. 3006-3024, December 2008.
3. M. Azin, D. J. Guggenmos, S. Barbay, R. J. Nudo, and P. Mohseni, "A battery-powered activity-dependent intracortical microstimulation IC for brain-machine-brain interface," *IEEE J. Solid-State Circuits*, vol. 46, no. 4, April 2011, In Press.
4. M. Azin, D. J. Guggenmos, S. Barbay, R. J. Nudo, and P. Mohseni, "An activity-dependent brain microstimulation SoC with integrated 23 nV/rtHz neural recording front-end and 750 nW spike discrimination processor," in *IEEE Symp. VLSI Circuits Dig. Papers*, Honolulu, Hi., Jun. 16-18, 2010, pp. 223-224.
5. M. Azin and P. Mohseni, "A high-output-impedance current microstimulator for anatomical rewiring of cortical circuitry," in *Proc. IEEE Int. Symp. Circuits and Systems (ISCAS '08)*, Seattle, Wash., May 18-21, 2008, pp. 2502-2505.
6. T. W. Berger et al., "Restoring lost cognitive function: Hippocampalcortical neural prostheses," *IEEE Eng. Med. Biol. Mag.*, vol. 24, no. 5, pp. 30-44, September/October 2005.
7. P. K. Campbell, K. E. Jones, R. J. Huber, K. W. Horch, and R. A. Normann, "A silicon-based, three-dimensional neural interface: Manufacturing process for an intracortical electrode array," *IEEE Trans. Biomed. Eng.*, vol. 38, pp. 758-767, 1991.
8. M. S. Chae, Z. Yang, M. R. Yuce, L. Hoang, and W. Liu, "A 128-channel 6-mW wireless neural recording IC with spike feature extraction and UWB transmitter," *IEEE Trans. Neural Syst. Rehab. Eng.*, vol. 17, no. 4, pp. 312-321, August 2009.
9. T. Chen, K. Chen, Z. Yang, K. Cockerham, and W. Liu, "A biomedical multiprocessor SoC for closed-loop neuro-prosthetic applications," in *IEEE Int. Solid State Circuits Conference (ISSCC '09) Dig. Tech. Papers*, San Francisco, Calif., Feb. 8-12, 2009, pp. 434-435.
10. T. G. Constandinou, J. Georgiou, and C. Toumazou, "A partial-current-steering biphasic stimulation driver for vestibular prostheses," *IEEE Trans. Biomed. Circuits Syst.*, vol. 2, no. 2, pp. 106-113, June 2008.
11. T. Denison, K. Consoer, W. Santa, A.-T. Avestruz, J. Cooley, and A. Kelly, "A 2 µW 100 nV/rtHz chopper-stabilized instrumentation amplifier for chronic measurement of neural field potentials," *IEEE J. Solid-State Circuits*, vol. 42, no. 12, pp. 2934-2945, December 2007.
12. X. J. Feng, B. Greenwald, H. Rabitz, E. Shea-Brown, and B. Kosut, "Toward closed-loop optimization of deep brain stimulation for Parkinson's disease: Concepts and lessons from a computational model," *J. Neural Eng.*, vol. 4, pp. L14-21, 2007.
13. M. Ghovanloo and K. Najafi, "A compact large-voltage-compliance high-output-impedance programmable current source for implantable microstimulators," *IEEE Trans. Biomed. Eng.*, vol. 52, no. 1, pp. 97-105, January 2005.
14. R. R. Harrison and C. Charles, "A low-power low-noise CMOS amplifier for neural recording applications," *IEEE J. Solid-State Circuits*, vol. 38, no. 6, pp. 958-965, June 2003.
15. L. R. Hochberg, M. D. Serruya, G. M. Friehs, J. A. Mukand, M. Saleh, A. H. Caplan, A. Branner, D. Chen, R. D. Penn, and J. P. Donoghue, "Neuronal ensemble control of prosthetic devices by a human with tetraplegia," *Nature*, vol. 442, pp. 164-171, July 2006.
16. A. Jackson, J. Mavoori, and E. E. Fetz, "Long-term motor cortex plasticity induced by an electronic neural implant," *Nature*, vol. 444, pp. 56-60, November 2006.
17. A. Jackson, C. T. Moritz, J. Mavoori, T. H. Lucas, and E. E. Fetz, "The neurochip BCI: Towards a neural prosthesis for upper limb function," *IEEE Trans. Neural Syst. Rehab. Eng.*, vol. 14, no. 2, pp. 187-190, June 2006.
18. A. Keller and H. Asanuma, "Synaptic relationships involving local axon collaterals of pyramidal neurons in the cat motor cortex," *J. Comp. Neurol.*, vol. 336, pp. 229-242, 1993.
19. J. Lee, H. G. Rhew, D. R. Kipke, and M. P. Flynn, "A 64-channel programmable closed-loop neurostimulator with 8-channel neural amplifier and logarithmic ADC," *IEEE J. Solid-State Circuits*, vol. 45, no. 9, pp. 1935-1945, September 2010.
20. X. Liu, A. Demosthenous, and N. Donaldson, "An integrated implantable stimulator that is fail-safe without off-chip blocking capacitors," *IEEE Trans. Biomed. Circuits Syst.*, vol. 2, no. 3, pp. 231-244, September 2008.

21. J. Mavoori, A. Jackson, C. Diorio, and E. Fetz, "An autonomous implantable computer for neural recording and stimulation in unrestrained primates," *J. Neurosci. Methods*, vol. 148, pp. 71-77, 2005.
22. D. J. McFarland and J. R. Wolpaw, "Brain-computer interface operation of robotic and prosthetic devices," *Computer*, vol. 41, no. 10, pp. 52-56, October 2008.
23. M. Mollazadeh, K. Murari, G. Cauwenberghs, and N. Thakor, "Micropower CMOS-integrated low-noise amplification, filtering, and digitization of multimodal neuropotentials," *IEEE Trans. Biomed. Circuits Syst.*, vol. 3, no. 1, pp. 1-10, February 2009.
24. C. T. Moritz, S. I. Perlmutter, and E. E. Fetz, "Direct control of paralyzed muscles by cortical neurons," *Nature*, vol. 456, pp. 639-643, 2008.
25. M. A. L. Nicolelis, A. A. Ghazanfar, B. M. Faggin, S. Votaw, and L. M. O. Oliveira, "Reconstructing the Engram: Simultaneous, multisite, many single neuron recordings," *Neuron*, vol. 18, pp. 529-537, April 1997.
26. M. Nishibe, S. Barbay, D. Guggenmos, and R. J. Nudo, "Reorganization of motor cortex after controlled cortical impact in rats and implications for functional recovery," *J. Neurotrauma*, vol. 27, pp. 2221-2232, December 2010.
27. M. Ortmanns, A. Rocke, M. Gehrke, and H. J. Tiedtke, "A 232-channel epiretinal stimulator ASIC," *IEEE J. Solid-State Circuits*, vol. 42, no. 12, pp. 2946-2959, December 2007.
28. J. P. Rauschecker and R. V. Shannon, "Sending sound to the brain," *Science*, vol. 295, no. 5557, pp. 1025-1029, February 2002.
29. F. Shahrokhi, K. Abdelhalim, D. Serletis, P. L. Carlen, and R. Genov, "The 128-channel fully differential integrated neural recording and stimulation interface," *IEEE Trans. Biomed. Circuits Syst.*, vol. 4, no. 3, pp. 149-161, June 2010.
30. J. J. Sit and R. Sarpeshkar, "A low-power blocking-capacitor-free charge-balanced electrode-stimulator chip with less than 6 nA dc error for 1-mA full-scale stimulation," *IEEE Trans. Biomed. Circuits Syst.*, vol. 1, no. 3, pp. 172-183, September 2007.
31. A. M. Sodagar, G. E. Perlin, Y. Yao, K. Najafi, and K. D. Wise, "An implantable 64-channel wireless microsystem for single-unit neural recording," *IEEE J. Solid-State Circuits*, vol. 44, no. 9, pp. 2591-2604, September 2009.
32. K. Sooksood, T. Stieglitz, and M. Ortmanns, "An active approach for charge balancing in functional electrical stimulation," *IEEE Trans. Biomed. Circuits Syst.*, vol. 4, no. 3, pp. 162-170, June 2010.
33. Y. Tsividis, *Operation and Modeling of the MOS Transistor*, 2nd ed. New York, N.Y.: Oxford Univ. Press, 1999.
34. B. K. Thurgood, D. J. Warren, N. M. Ledbetter, G. A. Clark, and R. R. Harrison, "A wireless integrated circuit for 100-channel charge-balanced neural stimulation," *IEEE Trans. Biomed. Circuits Syst.*, vol. 3, no. 6, pp. 405-414, December 2009.
35. M. Velliste, S. Perel, M. C. Spalding, A. S. Whitford, and A. B. Schwartz, "Cortical control of a prosthetic arm for self-feeding," *Nature*, vol. 453, pp. 1098-1101, June 2008.
36. S. Venkatraman, K. Elkabany, J. D. Long, Y. Yao, and J. M. Carmena, "A system for neural recording and closed-loop intracortical microstimulation in awake rodents," *IEEE Trans. Biomed. Eng.*, vol. 56, no. 1, pp. 15-22, January 2009.

What is claimed is:

1. A method comprising:
  detecting a first neural spike over a first channel and a second neural spike over a second channel in a first neural site at a first time using a chronically implanted microelectrode having a plurality of recording sites operably connected to a recording front-end and a processor unit of a neural prosthetic device, the recording front-end comprising a plurality of recording channels; and
  determining if the first neural spike received over the first channel and the second neural spike received over the second channel are acceptable neural spikes at the first time using a spike discriminator, a spike discrimination algorithm, and decision circuitry, wherein the spike discriminator and the spike discrimination algorithm identify acceptable neural spikes according to satisfaction of amplitude—and time-domain criteria at the first time, and the decision circuitry further identifies acceptable neural spikes by asking that the amplitude—and time-domain criteria be met on more than one recording channel at the first time; and
  if the first neural spike and the second neural spike are acceptable neural spikes, providing a stimulus to a second neural site within a defined period of time after the detection of the first neural spike using a stimulus delivering back-end, the first neural site and the second neural site being located within a subject having a brain injury in which there is substantially no effective communication between the first neural site and the second neural site.

2. The method of claim 1 continuing the detecting and delivering to a selected stage of functional recovery.

3. The method of claim 2 wherein the selected stage of functional recovery is reconnection of fibers, creation of a functional connection, or functional recovery of the subject.

4. The method of claim 1 wherein the first neural site and the second neural site are in different functional areas of the cortex.

5. A method comprising:
  detecting a first neural spike over a first channel and a second neural spike over a second channel in a first region of the brain at a first time in a subject using a microelectrode having a plurality of recording sites and a recording front-end having a plurality of recording channels;
  determining if the first neural spike received over the first channel and the second neural spike received over the second channel are acceptable neural spikes at the first time according to pre-selected criteria; and
  if the first neural spike and the second neural spike are acceptable, delivering a stimulus to a second region of the brain in the subject within a defined period of time after the detection of the first neural spike, wherein the first region of the brain is the frontal cortex and the second region of the brain is the parietal cortex.

6. The method of claim 5, wherein the first region of the brain is the motor area and the second region of the brain is the somatosensory area.

7. The method of claim 6, wherein the first region of the brain is the rostral forelimb area (RFA) and the second region of the brain is the somatic sensory cortex (SI).

8. A method comprising:
  detecting a first neural spike in a first channel and a second neural spike over a second channel in a first region of the brain at a first time in a subject using a microelectrode having a plurality of recording sites and a recording front-end having a plurality of recording channels;
  determining if the first neural spike received over the first channel and the second neural spike received over the second channel are acceptable neural spikes at the first time according to pre-selected criteria; and if the first neural spike and the second neural spike are acceptable, delivering a stimulus to a second region of the brain in the subject within a defined period of time after the detection of the first neural spike, wherein there is substantially no effective communication between the first and second regions of the brain, such that the detecting and delivering form a closed loop operation.

9. The method of claim 8 continuing the detecting and delivering to a selected stage of functional recovery.

10. The method of claim 9 wherein the selected stage of functional recovery is reconnection of fibers, creation of a functional connection, or functional recovery of the subject.

11. The method of claim 8 wherein the stimulus is an electrical pulse.

12. The method of claim 11 wherein the electrical pulse is monophasic or biphasic.

13. The method of claim 8 further comprising:
using a neural prosthetic device to deliver the stimulus to the second region of the brain,
wherein the neural prosthetic device comprises an integrated circuit that comprises:
a processor unit and a stimulus delivering back-end comprising a plurality of stimulation channels.

14. The method of claim 8 wherein delivering the stimulus occurs less than 1000 ms after a neural spike is detected in the first region of the brain.

15. The method of claim 8 wherein the first region of the brain, the second region of the brain, or both are located in a cortical region of the subject.

16. The method of claim 8 wherein the first region of the brain and the second region of the brain are in different functional areas of the cortex.

17. The method of claim 8 wherein the subject has an injury as a result of a stroke, a traumatic brain injury, a neurosurgical resection, a tumor, or epilepsy.

18. The method of claim 8, wherein the subject is ambulatory.

19. The method of claim 8, wherein the microelectrodes are chronically implanted for a period of at least 14 days.

20. A neural prosthetic device comprising:
an integrated circuit that comprises:
a recording front-end comprising a plurality of recording channels;
a recording microelectrode having a plurality of recording sites operably connected to the plurality of recording channels of the recording front-end of the integrated circuit;
a stimulus delivering back-end; and
a processor unit comprising a spike discriminator and decision circuitry that identify acceptable neural spikes, wherein the spike discriminator and decision circuitry identify acceptable neural spikes by:
detecting a first neural spike over a first channel and a second neural spike over a second channel in a first region of the brain at a first time;
determining if the first neural spike received over the first channel and the second neural spike received over the second channel are acceptable neural spikes at the first time according to pre-selected criteria; and
if the first neural spike and the second neural spike are acceptable, delivering a stimulus to a second region of the brain in a subject using the stimulus delivering back end within a defined period of time after the detection of the first neural spike, wherein there is substantially no effective communication between the first and second regions of the brain, such that the detecting and delivering form a closed loop operation.

21. The device of claim 20, wherein the spike discriminator identifies acceptable neural spikes according to amplitude— and time-domain criteria, and wherein the decision circuitry further identifies acceptable neural spikes by asking that the amplitude—and time-domain criteria be met on more than one recording channel.

22. The device of claim 20 further comprising a stimulation microelectrodes having a plurality of stimulating sites operably connected to the stimulus delivering back-end of the integrated circuit.

23. The device of claim 20 wherein the spike discriminator and decision circuitry utilize adjustable, user-set parameters.

24. The device of claim 20 further comprising a power supply operably connected to the stimulus delivering back-end.

25. The device of claim 20 wherein the processor unit is a digital signal processor unit.

26. The device of claim 20 wherein the recording front-end further comprises a low-noise amplifier, a highpass filter, a secondary amplifier and an analog-to-digital converter.

27. The device of claim 20 wherein the stimulus delivering back-end further comprises a stimulator timing control, a signal level shifter, and a digital-to-analog converter.

28. The device of claim 20 further comprising a radio-frequency transmitter.

* * * * *